(12) United States Patent
Slayton et al.

(10) Patent No.: US 10,183,182 B2
(45) Date of Patent: Jan. 22, 2019

(54) METHODS AND SYSTEMS FOR TREATING PLANTAR FASCIA

(75) Inventors: Michael H. Slayton, Tempe, AZ (US); Peter G. Barthe, Phoenix, AZ (US)

(73) Assignee: Guided Therapy Systems, LLC, Mesa, AZ (US)

(*) Notice: Subject to any disclaimer, the term of this patent is extended or adjusted under 35 U.S.C. 154(b) by 0 days.

(21) Appl. No.: 13/136,541

(22) Filed: Aug. 2, 2011

(65) Prior Publication Data

US 2012/0143056 A1 Jun. 7, 2012

Related U.S. Application Data

(60) Provisional application No. 61/369,782, filed on Aug. 2, 2010, provisional application No. 61/369,793, filed (Continued)

(51) Int. Cl.
*A61N 7/00* (2006.01)
*A61N 7/02* (2006.01)
(Continued)

(52) U.S. Cl.
CPC .................. *A61N 7/00* (2013.01); *A61B 8/13* (2013.01); *A61B 8/14* (2013.01); *A61B 8/4254* (2013.01); *A61B 8/5246* (2013.01); *A61B 17/320068* (2013.01); *A61N 7/02* (2013.01); *A61B 8/4272* (2013.01); *A61B 8/485* (2013.01); *A61B 2018/00642* (2013.01); *A61B 2018/00898* (2013.01); *A61B 2090/378* (2016.02); *A61N 2007/006* (2013.01); (Continued)

(58) Field of Classification Search
CPC .............................. A61N 7/00; A61H 23/0245

USPC ............................................................ 601/2
See application file for complete search history.

(56) References Cited

U.S. PATENT DOCUMENTS 2,427,348 A 9/1947 Bond et al.
3,913,386 A 10/1975 Saglio
(Continued)

FOREIGN PATENT DOCUMENTS

CA 2580561 9/2005
CA 2580720 9/2005
(Continued)

OTHER PUBLICATIONS

Renata Graciele Zanon, Adriana Kundrat Brasil, Marta Imamura, Continuous Ultrasound for Chronic Plantar Fasciitis Treatment, ACTA ORTOP BRAS 14(3)—2006, pp. 137-140.*
(Continued)

*Primary Examiner* — Hien Nguyen
(74) *Attorney, Agent, or Firm* — Quarles & Brady, LLP

(57) ABSTRACT

Various embodiments, described herein, provide methods and systems for the treatment of plantar fascia. In some embodiments, a method of non-invasive treatment of plantar fasciacan include the steps of identifying a damage location comprising a planter fascia; directing a conformal distribution of ultrasound energy to the plantar fascia at the damage location; creating a plurality of micro lesions in the plantar fascia at the damage location; initiating healing of a plurality of micro tears in the plantar fascia at the damage location; and sparing intervening tissue between the plantar fascia and a surface of a sole of a foot.

18 Claims, 10 Drawing Sheets

Related U.S. Application Data on Aug. 2, 2010, provisional application No. 61/369,806, filed on Aug. 2, 2010, provisional application No. 61/370,095, filed on Aug. 2, 2010.

(51) Int. Cl.
| | | |
|---|---|---|
| *A61B 8/14* | (2006.01) | |
| *A61B 8/00* | (2006.01) | |
| *A61B 8/13* | (2006.01) | |
| *A61B 17/32* | (2006.01) | |
| *A61B 18/00* | (2006.01) | |
| *A61B 8/08* | (2006.01) | |
| *A61B 90/00* | (2016.01) | |

(52) U.S. Cl.
CPC ............... *A61N 2007/0013* (2013.01); *A61N 2007/0034* (2013.01); *A61N 2007/0052* (2013.01); *A61N 2007/0065* (2013.01); *A61N 2007/0091* (2013.01); *A61N 2007/0095* (2013.01); *A61N 2007/027* (2013.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Brisken et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fly et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlaeger et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger |
| 5,371,483 A | 12/1994 | Bhardwaj |
| 5,375,602 A | 12/1994 | Lancee et al. |
| 5,380,280 A | 1/1995 | Peterson |
| 5,380,519 A | 1/1995 | Schneider et al. |
| 5,391,140 A | 2/1995 | Schaetzle |
| 5,391,197 A | 2/1995 | Burdette et al. |
| 5,392,259 A | 2/1995 | Bolorforosh |

(56) References Cited

U.S. PATENT DOCUMENTS

| | | |
|---|---|---|
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder |
| 5,423,220 A | 6/1995 | Finsterwald et al. |
| 5,435,311 A | 7/1995 | Umemura |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,488 A | 12/1995 | Fujio |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,676,692 A | 10/1997 | Sanghvi |
| 5,685,820 A | 11/1997 | Riek et al. |
| 5,687,737 A | 11/1997 | Branham et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,839,751 A | 11/1998 | Bonin |
| 5,840,032 A | 11/1998 | Hatfield et al. |
| 5,844,140 A | 12/1998 | Seale |
| 5,853,367 A | 12/1998 | Chalek et al. |
| 5,871,524 A | 2/1999 | Knowlton |
| 5,873,902 A | 2/1999 | Sanghvi |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,882 A | 11/1999 | Rosenchein |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,883 A | 7/2000 | Sanghvi |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |

(56) References Cited

U.S. PATENT DOCUMENTS

| | | |
|---|---|---|
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Digs |
| 6,190,336 B1 | 2/2001 | Duarte |
| 6,193,658 B1 | 2/2001 | Wendelken et al. |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,088 B1 * | 6/2001 | Kaufman et al. ............... 601/2 |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,296,619 B1 | 10/2001 | Brisken |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Veazy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Constantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe |
| 6,499,485 B1 * | 12/2002 | Pepera ............... A61F 7/02 128/845 |
| 6,500,121 B1 | 12/2002 | Slayton |
| 6,500,141 B1 | 12/2002 | Irion |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk et al. |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller et al. |
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,825,176 B2 | 4/2004 | Mourad |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,887,239 B2 | 5/2005 | Elstrom |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,960,173 B2 * | 11/2005 | Babaev ............... 601/2 |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |

(56) References Cited

U.S. PATENT DOCUMENTS

| | | |
|---|---|---|
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,235,909 B2 | 8/2012 | Barthe et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 2001/0009997 A1 | 7/2001 | Pope |
| 2001/0009999 A1* | 7/2001 | Kaufman et al. ............... 606/32 |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0060736 A1 | 2/2003 | Martin et al. |
| 2003/0050678 A1 | 3/2003 | Sierra |
| 2003/0055417 A1 | 3/2003 | Truckai et al. |
| 2003/0040442 A1 | 4/2003 | Ishidera |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom et al. |
| 2004/0041563 A1 | 3/2004 | Lewin et al. |
| 2004/0042168 A1 | 3/2004 | Yang et al. |
| 2004/0044375 A1 | 3/2004 | Diederich et al. |

(56) References Cited

U.S. PATENT DOCUMENTS

| | | |
|---|---|---|
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishbashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0249318 A1 | 9/2004 | Tanaka |
| 2004/0206365 A1 | 10/2004 | Knowlton |
| 2004/0210214 A1 | 10/2004 | Knowlton |
| 2004/0041880 A1 | 11/2004 | Brisken et al. |
| 2004/0217675 A1 | 11/2004 | Desilets |
| 2004/0254620 A1 | 12/2004 | Lacoste et al. |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1* | 4/2006 | Slayton et al. ............... 600/439 |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1* | 6/2006 | Slayton et al. ............... 600/439 |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1* | 8/2006 | Grossman ....................... 606/32 |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0261584 A1 | 11/2006 | Eshel |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1* | 3/2007 | Johnson ....................... 424/93.7 |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0166357 A1* | 7/2007 | Shaffer et al. ................. 424/443 |
| 2007/0167709 A1 | 7/2007 | Slayton |
| 2007/0208253 A1 | 9/2007 | Slayton |
| 2007/0213792 A1* | 9/2007 | Yaroslaysky et al. ......... 607/100 |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pederson |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0254006 A1* | 10/2009 | Babaev ............................. 601/2 |

(56) References Cited

U.S. PATENT DOCUMENTS

| | | | |
|---|---|---|---|
| 2009/0299175 A1 | 12/2009 | Bernstein et al. | |
| 2009/0318909 A1 | 12/2009 | Debenedictis et al. | |
| 2010/0011236 A1 | 1/2010 | Barthe et al. | |
| 2010/0022919 A1 | 1/2010 | Peterson | |
| 2010/0022922 A1 | 1/2010 | Barthe et al. | |
| 2010/0042020 A1 | 2/2010 | Ben-Ezra | |
| 2010/0049178 A1 | 2/2010 | Deem et al. | |
| 2010/0063422 A1 | 3/2010 | Hynynen et al. | |
| 2010/0130891 A1 | 5/2010 | Taggart et al. | |
| 2010/0160782 A1 | 6/2010 | Slayton et al. | |
| 2010/0160837 A1 | 6/2010 | Hunziker et al. | |
| 2010/0168576 A1* | 7/2010 | Poland et al. | 600/443 |
| 2010/0191120 A1 | 7/2010 | Kraus et al. | |
| 2010/0241035 A1 | 9/2010 | Barthe et al. | |
| 2010/0280420 A1 | 11/2010 | Barthe et al. | |
| 2010/0286518 A1 | 11/2010 | Lee et al. | |
| 2011/0040171 A1 | 2/2011 | Foley et al. | |
| 2011/0040190 A1 | 2/2011 | Jahnke et al. | |
| 2011/0087099 A1 | 4/2011 | Eshel et al. | |
| 2011/0087255 A1* | 4/2011 | McCormack et al. | 606/167 |
| 2011/0112405 A1 | 5/2011 | Barthe et al. | |
| 2011/0178444 A1 | 7/2011 | Slayton et al. | |
| 2011/0190745 A1 | 8/2011 | Uebelhoer et al. | |
| 2011/0264012 A1 | 10/2011 | Lautzenhiser et al. | |
| 2012/0004549 A1 | 1/2012 | Barthe et al. | |
| 2012/0016239 A1 | 1/2012 | Barthe et al. | |
| 2012/0029353 A1 | 2/2012 | Slayton et al. | |
| 2012/0035475 A1 | 2/2012 | Barthe et al. | |
| 2012/0035476 A1 | 2/2012 | Barthe et al. | |
| 2012/0046547 A1 | 2/2012 | Barthe et al. | |
| 2012/0053458 A1 | 3/2012 | Barthe et al. | |
| 2012/0111339 A1 | 5/2012 | Barthe et al. | |
| 2012/0143056 A1 | 6/2012 | Slayton et al. | |
| 2012/0165668 A1 | 6/2012 | Slayton et al. | |
| 2012/0165848 A1 | 6/2012 | Slayton et al. | |
| 2012/0197120 A1 | 8/2012 | Makin et al. | |
| 2012/0197121 A1 | 8/2012 | Slayton et al. | |
| 2012/0215105 A1 | 8/2012 | Slayton et al. | |
| 2012/0271294 A1 | 10/2012 | Barthe et al. | |
| 2012/0296240 A1 | 11/2012 | Azhari et al. | |
| 2012/0316426 A1 | 12/2012 | Foley et al. | |
| 2012/0330197 A1 | 12/2012 | Makin et al. | |
| 2012/0330222 A1 | 12/2012 | Barthe et al. | |
| 2012/0330223 A1 | 12/2012 | Makin et al. | |
| 2013/0012755 A1 | 1/2013 | Slayton | |
| 2013/0012816 A1 | 1/2013 | Slayton et al. | |
| 2013/0012838 A1 | 1/2013 | Jaeger et al. | |
| 2013/0012842 A1 | 1/2013 | Barthe | |
| 2013/0018286 A1 | 1/2013 | Slayton et al. | |
| 2013/0046209 A1 | 2/2013 | Slayton et al. | |
| 2013/0066208 A1 | 3/2013 | Barthe et al. | |
| 2013/0066237 A1 | 3/2013 | Smotrich et al. | |
| 2013/0072826 A1 | 3/2013 | Slayton et al. | |
| 2013/0096471 A1 | 4/2013 | Slayton et al. | |
| 2013/0190659 A1 | 7/2013 | Slayton et al. | |
| 2013/0211258 A1 | 8/2013 | Barthe et al. | |
| 2013/0281853 A1 | 10/2013 | Slayton et al. | |
| 2013/0281891 A1 | 10/2013 | Slayton et al. | |
| 2013/0296697 A1 | 11/2013 | Slayton et al. | |
| 2013/0296700 A1 | 11/2013 | Slayton et al. | |
| 2013/0303904 A1 | 11/2013 | Barthe et al. | |
| 2013/0303905 A1 | 11/2013 | Barthe et al. | |
| 2013/0310863 A1 | 11/2013 | Barthe et al. | |
| 2014/0082907 A1 | 3/2014 | Barthe | |
| 2014/0142430 A1 | 5/2014 | Slayton et al. | |
| 2014/0148834 A1 | 5/2014 | Barthe et al. | |
| 2014/0180174 A1 | 6/2014 | Slayton et al. | |
| 2014/0187944 A1 | 7/2014 | Slayton et al. | |
| 2014/0188015 A1 | 7/2014 | Slayton et al. | |
| 2014/0188145 A1 | 7/2014 | Slayton et al. | |

FOREIGN PATENT DOCUMENTS

| | | |
|---|---|---|
| CA | 2583552 | 10/2005 |
| CA | 2583600 | 4/2007 |
| CA | 2583641 | 4/2007 |
| CA | 2723791 | 5/2008 |
| CA | 2748362 | 6/2011 |
| DE | 4029175 | 3/1992 |
| DE | 10140064 | 3/2003 |
| DE | 10219217 | 11/2003 |
| DE | 10219297 | 11/2003 |
| DE | 20314479 | 3/2004 |
| DE | 202005022062 | 12/2012 |
| EP | 0344773 | 12/1989 |
| EP | 1479412 | 11/1991 |
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1374944 A | 1/2004 |
| EP | 05798325.6 | 4/2007 |
| EP | 05798870.1 | 4/2007 |
| EP | 05805833.0 | 7/2007 |
| EP | 05808908.7 | 7/2007 |
| EP | 05810308.6 | 7/2007 |
| EP | 06751473.7 | 11/2007 |
| EP | 07814933.3 | 4/2009 |
| EP | 0785548.1 | 7/2009 |
| EP | 0874801.2 | 12/2009 |
| EP | 08747803.8 | 12/2009 |
| EP | 08755129.7 | 12/2009 |
| EP | 10185009.7 | 10/2010 |
| EP | 10185100.4 | 10/2010 |
| EP | 10185112.9 | 10/2010 |
| EP | 10185117.8 | 10/2010 |
| EP | 5808908.7 | 6/2011 |
| EP | 11172024.9 | 6/2011 |
| EP | 11172025.6 | 6/2011 |
| EP | 11172026.4 | 6/2011 |
| EP | 09835856.7 | 8/2011 |
| EP | 12156419.9 | 1/2012 |
| EP | 12178124.9 | 7/2012 |
| GB | 2113099 | 8/1983 |
| HK | 8106764.3 | 7/2007 |
| HK | 8105587 | 5/2008 |
| HK | 8106763.4 | 6/2008 |
| IL | 181892 | 3/2007 |
| IL | 181895 | 3/2007 |
| IL | 182187 | 3/2007 |
| IL | 182189 | 3/2007 |
| IL | 182188 | 5/2007 |
| IL | 10-2007-7007966 | 10/2007 |
| IL | 201942 | 11/2009 |
| IL | 201944 | 11/2009 |
| IL | 221649 | 8/2011 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2007-535860 | 10/2005 |
| JP | 2007-535865 | 10/2005 |
| JP | 2007-535880 | 10/2005 |
| JP | 2005323213 | 11/2005 |

(56) References Cited

FOREIGN PATENT DOCUMENTS

| | | |
|---|---|---|
| JP | 2006520247 | 9/2006 |
| JP | 2007-532508 | 3/2007 |
| JP | 2007-533694 | 3/2007 |
| JP | 2007505793 A | 3/2007 |
| JP | 2009-529330 | 3/2009 |
| JP | 2009518126 | 5/2009 |
| JP | 2010-526589 | 11/2009 |
| JP | 2010517695 | 5/2010 |
| JP | 2011-543684 | 6/2011 |
| JP | 4695188 | 6/2011 |
| JP | 2011-169651 | 8/2011 |
| JP | 2011-209922 | 9/2011 |
| JP | 2011-234216 | 10/2011 |
| JP | 2012-10425 | 1/2012 |
| KR | 1020010024871 | 3/2001 |
| KR | 1020060113930 | 11/2006 |
| KR | 10-2007-7006124 | 3/2007 |
| KR | 10-2007-7006495 | 3/2007 |
| KR | 10-2007-7007963 | 4/2007 |
| KR | 10-2007-7707969 | 4/2007 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 10-2011-7016330 | 6/2011 |
| KR | 10-2011-7017978 | 7/2011 |
| KR | 10-2011-7017980 | 7/2011 |
| KR | 10-2011-7017981 | 7/2011 |
| KR | 10-2011-7017982 | 7/2011 |
| TW | 97116816 | 5/2008 |
| TW | 97116818 | 5/2008 |
| WO | 9625888 | 8/1996 |
| WO | 9639079 A1 | 12/1996 |
| WO | 9735518 | 10/1997 |
| WO | 9832379 | 7/1998 |
| WO | 9933520 | 7/1999 |
| WO | 9949788 | 10/1999 |
| WO | 0006032 | 2/2000 |
| WO | 0015300 | 3/2000 |
| WO | 0021612 | 4/2000 |
| WO | 0053113 | 9/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 02024050 | 3/2002 |
| WO | 020292168 | 11/2002 |
| WO | 03053266 A | 7/2003 |
| WO | 03065347 | 8/2003 |
| WO | 03070105 | 8/2003 |
| WO | 03077833 | 8/2003 |
| WO | 03086215 | 10/2003 |
| WO | 03096883 | 11/2003 |
| WO | 03099177 | 12/2003 |
| WO | 03101530 | 12/2003 |
| WO | 2004000116 A | 12/2003 |
| WO | 2004080147 | 9/2004 |
| WO | 2004110558 | 12/2004 |
| WO | 2005011804 A | 2/2005 |
| WO | 2005065408 | 7/2005 |
| WO | 2005090978 | 9/2005 |
| WO | PCT/US05/33046 | 9/2005 |
| WO | PCT/US05/33195 | 9/2005 |
| WO | PCT/US05/34358 | 9/2005 |
| WO | PCT/US05/36269 | 10/2005 |
| WO | PCT/US05/36377 | 10/2005 |
| WO | PCT/US2005/36253 | 10/2005 |
| WO | 2006036870 | 4/2006 |
| WO | 2006042163 A | 4/2006 |
| WO | 2006042168 | 4/2006 |
| WO | 2006042201 | 4/2006 |
| WO | PCT/2006/015779 | 4/2006 |
| WO | 2006065671 | 6/2006 |
| WO | 2006082573 | 8/2006 |
| WO | 2007067563 A | 6/2007 |
| WO | PCT/US07/78712 | 9/2007 |
| WO | PCT/US2007/78945 | 9/2007 |
| WO | 2008024923 A2 | 2/2008 |
| WO | 2008036622 A | 3/2008 |
| WO | PCT/US08/62930 | 5/2008 |
| WO | PCT/US08/62932 | 5/2008 |
| WO | PCT/US08/62936 | 5/2008 |
| WO | 2009013729 | 1/2009 |
| WO | PCT/US09/46475 | 6/2009 |
| WO | PCT/US08/62932 | 11/2009 |
| WO | 2009149390 A1 | 12/2009 |
| WO | PCT/US09/69467 | 12/2009 |
| WO | PCT/US11/001361 | 8/2011 |
| WO | PCT/US11/001362 | 8/2011 |
| WO | PCT/US11/001366 | 8/2011 |
| WO | PCT/US11/001367 | 8/2011 |
| WO | PCT/US12/046122 | 7/2012 |
| WO | PCT/US12/46123 | 7/2012 |
| WO | PCT/US12/46125 | 7/2012 |
| WO | PCT/US12/046327 | 7/2012 |
| WO | 2014055708 A1 | 4/2014 |

OTHER PUBLICATIONS

Fay Crawford, Michael Snaith, How effective is therapeutic ultrasound in the treatment of heel pain, 1996, Annals of the Rheumatic Diseases, 55, pp. 265-267.*

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Barthe et al., "Ultrasound therapy system and abiation results utilizing miniature imaging/therapy arrays," Ultrasonics Symposium, 2004 IEEE, Aug. 23, 2004, pp. 1792-1795, vol. 3.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

(56) References Cited

OTHER PUBLICATIONS

Makin et al, "Miniaturized Ultrasound Arrays for Interstitial Ablation and Imaging," UltraSound Med. Biol. 2005, Nov. 1, 2005, pp. 1539-1550, vol. 31(11).
Makin et al., "Confirmal Bulk Ablation and Therapy Monitoring Using Intracorporeal Image-Treat Ultrasound Arrays", 4th International Symposium on Therapeutic Ultrasound, Sep. 19, 2004.
Manohar et al, "Photoaccoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling nad Experiments," J. Acoust. Soc. Am., Oct. 1, 2005, pp. 2715-2724, vol. 118(4).
Paradossi et al., "Poly(vinyl alcohol) as versatile biomaterial for potential biomedical applications," Journal of Materials Science: Materials in Medicine, 2003, pp. 687-691, vol. 14.
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-Induced Lesions in Canine Livers," 1999, Ultrasound in Med & Bio, vol. 25, No. 7, pp. 1099-1113.
Mitragotri, Samir; "Healing sound: the use of ultrasound in drug delivery and other therapeutic applications," Nature Reviews; Drug Delivery, pp. 255-260, vol. 4.
Sanghvi, N.T., et al., "Transrectal Ablation of Prostrate Tissue Using Focused Ultrasound," 1993 Ultrasonics Symposium, IEEE, pp. 1207-1210.
Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.
Ueno, S., et al., "Ultrasound Thermometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.
Sassen, Sander, "ATI's R520 architecture, the new king of the hill?" http://www.hardwareanalysis.com/content/article/1813, Sep. 16, 2005, 2 pages.
Wasson, Scott, "NVIDIA's GeFroce 7800 GTX graphics processor Power MADD," http://techreport.com/reviews/2005q2/geforce-7800gtx/index.x?pg=1, Jun. 22, 2005, 4 pages.
Chen, L. et al., ""Effect of Blood Perfusion on the ablation of liver perenchyma with high intensity focused ultrasound,"" Phys. Med. Biol; 38:1661-1673; 1993b.
Damianou et al., Application of the Thermal Dose Concept for Predicting the Necrosed Tissue Volume During Ultrasound Surgery, 1993 IEEE Ultrasound Symposium, pp. 1199-1202.
Fry, W.J. et al., "Production of Focal Destructive Lesions in the Central Nervous System with Ultrasound," J. Neurosurg., 11:471-478; 1954.

Jeffers et al., "Evaluation of the Effect of Cavitation Activity on Drug-Ultrasound Synergisms," 1993 IEEE Ultrasonics Symposium, pp. 925-928.
Madersbacher, S. et al., "Tissue Ablation in Bening Prostatic Hyperplasia with High Intensity Focused Ultrasound," Dur. Urol., 23 (suppl. 1):39-43; 1993.
Saad et al., "Ultrasound-Enhanced Effects of Adriamycin Against Murine Tumors," Ultrasound in Med. & Biol. vol. 18, No. 8, pp. 715-723 (1992).
Simon et al., "Applications of Lipid-Coated Microbubble Ultrasonic Contrast to Tumor Therapy," Ultrasound in Med. & Biol. vol. 19, No. 2, pp. 123-125 (1993).
Tata et al., "Interaction of Ultrasound and Model Membrane Systems: Analyses and Predictions," American Chemical Society, Phys. Chem. 1992, 96, pp. 3548-3555.
Arthur et al., "Non-invasive estimation of hyperthermia temperatures with ultrasound," Int. J. Hyperthermia, Sep. 2005, 21(6), pp. 589-600.
International Search Report and Written Opinion dated Apr. 6, 2012 in Application No. PCT/US2011/001367.
U.S. Appl. No. 09/443,760, filed Nov. 19, 1999, Imaging, Therapy and Temperature Monitoring Ultrasonic System.
U.S. Appl. No. 11/744,655, filed May 4, 2007, Imaging, Therapy and Temperature Monitoring Ultrasonic System.
U.S. Appl. No. 08/943,728, filed Oct. 3, 1997, Drug Carrier.
U.S. Appl. No. 13/071,298, filed Mar. 24, 2011, Visual Imaging System for Ultrasonic Probe.
U.S. Appl. No. 12/135,962, filed Jun. 9, 2008, Method and System for Ultrasound Treatment with a Multi-Directional Transducer.
U.S. Appl. No. 13/294,004, filed Nov. 10, 2011, Method and System for Ultrasound Treatment with a Multi-Directional Transducer.
U.S. Appl. No. 12/792,934, filed Jun. 3, 2010, System and Method for Ultra-High Frequency Ultrasound Treatment.
U.S. Appl. No. 12/834,754, filed Jul. 10, 2010, System and Method for Variable Depth Ultrasound Treatment.
U.S. Appl. No. 13/564,552, filed Aug. 1, 2012, Method and System for Three-Dimensional Scanning and Imaging.
U.S. Appl. No. 12/437,726, filed May 8, 2009, Method and System for Combined Ultrasound Treatment.
U.S. Appl. No. 11/163,148, filed Oct. 6, 2005, Method and System for Controlled Thermal Injury of Human Superficial Tissue.
U.S. Appl. No. 13/444,688, filed Apr. 11, 2012, Method and System for Controlled Thermal Injury of Human Superficial Tissue.
U.S. Appl. No. 12/415,945, filed Mar. 31, 2009, Method and System for Noninvasive Mastopexy.
U.S. Appl. No. 11/163,152, filed Oct. 6, 2005, Method and System for Treatment of Sweat Glands.
U.S. Appl. No. 13/603,279, filed Sep. 4, 2012, Method for Treatment of Sweat Hyperhidrosis.
U.S. Appl. No. 11/163,154, filed Oct. 6, 2005, Method and System for Treating Cellulite.
U.S. Appl. No. 13/356,405, filed Jan. 23, 2012, Method and System for Treating Cellulite.
U.S. Appl. No. 11/163,151, filed Oct. 6, 2005, Method and System for Noninvasive Face Lifts and Deep Tissue Tightening.
U.S. Appl. No. 12/028,636, filed Feb. 8, 2008, Method and System for Noninvasive Face Lifts and Deep Tissue Tightening.
U.S. Appl. No. 13/444,485, filed Apr. 11, 2012, Treatment of Sub-dermal regions for Cosmetic Effects.
U.S. Appl. No. 13/230,498, filed Sep. 12, 2011, Method and System for Photoaged Tissue.
U.S. Appl. No. 11/163,176, filed Oct. 7, 2005, Method and System for Treating Blood Vessel Disorders.
U.S. Appl. No. 13/601,742, filed Aug. 31, 2012, Method for Treating Blood Vessel Disorders.
U.S. Appl. No. 12/350,383, filed Jan. 8, 2009, Method and System for Treating Acne and Sebaceous Glands.
U.S. Appl. No. 12/574,512, filed Oct. 6, 2009, Method and system for treating stretch marks.
U.S. Appl. No. 13/453,487, filed Apr. 23, 2012, Method and System for Enhancing Computer Peripheral Safety.

(56) References Cited

OTHER PUBLICATIONS

U.S. Appl. No. 11/538,794, filed Oct. 4, 2006, Ultrasound System and Method for Imaging and/or Measuring Displacement of Moving Tissue and Fluid.
U.S. Appl. No. 11/738,682, filed Apr. 23, 2007, Method and System for Non-Ablative Acne Treatment and Prevention.
U.S. Appl. No. 11/857,989, filed Sep. 19, 2007, Method and System for Treating Muscle, Tendon, Ligament and Cartilage Tissue.
U.S. Appl. No. 13/494,856, filed Jun. 12, 2012, Method and System for Treating Muscle, Tendon, Ligament and Cartilage Tissue.
U.S. Appl. No. 12/116,845, filed May 7, 2008, Method and System for Combined Energy Therapy Profile.
U.S. Appl. No. 12/116,810, filed May 7, 2008, Methods and Systems for Modulation Medicants Using Acoustic Energy.
U.S. Appl. No. 12/116,828, filed May 7, 2008, Methods and Systems for Coupling and Focusing Acoustic Energy Using a Coupler Member.
U.S. Appl. No. 12/954,484, filed Nov. 24, 2010, Methods and Systems for Generating Thermal Bubbles for Improved Ultrasound Imaging and Therapy.
U.S. Appl. No. 12/646,609, filed Dec. 23, 2009, Methods for Fat Reduction and/or Cellulite Treatment.
U.S. Appl. No. 13/136,538, filed Aug. 2, 2011, Systems and Methods for Treating Acute and/or Chronic Injuries in Soft Tissue.
U.S. Appl. No. 13/136,542, filed Aug. 2, 2011, Systems and Methods for Treating Cartilage.
U.S. Appl. No. 13/136,541, filed Aug. 2, 2011, Methods and Systems for Treating Plantar Fascia.
U.S. Appl. No. 13/136,544, filed Aug. 2, 2011, Systems and Methods for Ultrasound Treatment.
U.S. Appl. No. 13/245,822, filed Sep. 26, 2011, System and Method for Cosmetic Treatment.
U.S. Appl. No. 13/245,852, filed Sep. 26, 2011, System for Cosmetic Treatment.
U.S. Appl. No. 13/245,864, filed Sep. 26, 2011, Method for Non-Invasive Cosmetic Treatment of the Eye Region.
U.S. Appl. No. 13/246,117, filed Sep. 27, 2011, Methods for Non-Invasive Lifting and Tightening off the Lower Face and Neck.
U.S. Appl. No. 13/245,112, filed Sep. 27, 2011, Tissue Imaging and Treatment Method.
Calderhead et al., One Mechanism Behind LED Photo-Therapy for Wound Healing and Skin Rejuvenation: Key Role of the Mast Cell, Laser Therapy, Jul. 2008, pp. 141-148, 17.3.
European Examination Report in related Application No. 09835856.7 dated Apr. 11, 2004.
International Search Report and Written Opinion dated Apr. 6, 2012 in Application No. PCT/US2011/001366.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
European Examination Report in related Application No. 05808908.7 dated Jun. 29, 2009.
European Examination Report in related Application No. 05810308.6 dated Jun. 29, 2009.
European Examination Report in related Application No. 10185100.4 dated Jan. 6, 2014.
European Examination Report in related Application No. 10185120.2 dated Jan. 22, 2014.
Decision of the Korean Intellectual Property Tribunal dated Jun. 28, 2013 regarding Korean Patent No. 10-1142108, which is the related to the pending application and/or an application identified in the Table on the pp. 2-5 of the information Disclosure Statement herein (English translation, English translation certification, and Korean decison included).
Harr, G.R. et al., "Tissue Destruction with Focused Ultrasound in Vivo," Eur. Urol. 23 (suppl. 1):8-11; 1993.
International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2012 in Application No. PCT/US2012/046327.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
PCT International Search Report and Written Opinion, PCT/US2014/030779, dated Sep. 1, 2014, 8 pages.
European Patent Office, Examination Report, EP 07814933.3, dated Aug. 5, 2014, 5 pages.
European Patent Office, Examination Report, EP 05798870.1, dated Oct. 20, 2014, 5 pages.
European Patent Office, Examination Report, EP 10185100.4, dated Oct. 24, 2014, 4 pages.
European Patent Office, Examination Report, EP 10185112.9, dated Oct. 24, 2014, 5 pages.
European Patent Office, Examination Report, EP 10185117.8, dated Oct. 24, 2014, 5 pages.
European Patent Office, Examination Report, EP 10185120.2, dated Oct. 24, 2014, 4 pages.
U.S. Appl. No. 13/380,936, filed Apr. 1, 2013, Visual Imaging System for Ultrasonic Probe.
U.S. Appl. No. 13/679,430, filed Nov. 16, 2012, Treatment of Sub-dermal regions for Cosmetic Effects.
U.S. Appl. No. 13/835,635, filed Mar. 15, 2013, Treatment of Sub-dermal regions for Cosmetic Effects.
U.S. Appl. No. 13/863,249, filed Apr. 15, 2013, System and Method for Cosmetic Treatment.
U.S. Appl. No. 13/863,281, filed Apr. 15, 2013, Systems for Non-invasive Cosmetic Treatment.
U.S. Appl. No. 13/545,945, filed Jul. 10, 2012, Systems and Methods for Treating Injuries to Joints and Connective Tissue.
U.S. Appl. No. 13/545,954, filed Jul. 10, 2012, Systems and Methods for Improving an Outside Appearance of Skin Using Ultrasound as an Energy Source.
U.S. Appl. No. 13/545,929, filed Jul. 10, 2012, Methods & Systems for Ultrasound Treatment.
U.S. Appl. No. 13/547,011, filed Jul. 10, 2012, Systems and Methods for Monitoring and Controlling Ultrasound Power Output and Stability.
U.S. Appl. No. 13/545,931, filed Jul. 10, 2012, Methods and Systems for Controlling Acoustic Energy Deposition into a Medium.
U.S. Appl. No. 13/547,023, filed Jul. 11, 2012, Systems and Methods for Coupling an Ultrasound Source to Tissue.

\* cited by examiner

METHODS AND SYSTEMS FOR TREATING PLANTAR FASCIA

CROSS-REFERENCE TO RELATED APPLICATIONS

This application claims priority to and the benefit of U.S. Provisional Patent Application Ser. No. 61/369,782, entitled "Systems and Methods for Ultrasound Treatment", filed Aug. 2, 2010; U.S. Provisional Patent Application Ser. No. 61/369,793, entitled "System and Method for Treating Sports Related Injuries", filed Aug. 2, 2010; U.S. Provisional Patent Application Ser. No. 61/369,806, entitled "System and Method for Treating Sports Related Injuries", filed Aug. 2, 2010; U.S. Provisional Patent Application Ser. No. 61/370,095, entitled "System and Method for Treating Cartilage", filed Aug. 2, 2010; all of which are incorporated by reference herein.

BACKGROUND

Plantar fasciitis involves pain and inflammation of a thick band of tissue, called the plantar fascia, which runs across the bottom of the foot and connects the heel bone to the toes. This band of tissue is what creates the arch of the foot.

Plantar fasciitis is one of the most common causes of heel pain. When the fascia is overstretched or overused, it can become inflamed. When the fascia is inflamed, it can be painful and make walking more difficult. Plantar fasciitis is irritation and swelling of the thick tissue on the bottom of the foot.

Treatment options for plantar fasciitis include rest, massage therapy, stretching, weight loss, night splints, motion control running shoes, physical therapy, cold therapy, heat therapy, orthotics, anti-inflammatory medications, injection of corticosteroids, and in some cases, surgery. However, these treatment options are not successful in all cases. Accordingly, new treatment options for plantar fasciitis are needed.

SUMMARY

Accordingly, various embodiments, described herein, provide methods and systems for the treatment of plantar fascia. In some embodiments, method of treating plantar fascia can include identifying a damage location comprising a planter fascia and surrounding tissue; directing a conformal distribution of ultrasound energy to the damage location; creating a conformal region of elevated temperature in the damage location; stimulating at least one biological effect in damage location; and reducing inflammation in the surrounding tissue.

Some embodiments provide a system for treating plantar fascia. The system can include a hand-held probe and a controller in communication with the hand held probe. In some embodiments, the hand-held probe can include a housing, which can contain an ultrasound transducer configured to focus a conformal distribution of ultrasound energy into a region of interest comprising a plantar fascia and surround subcutaneous tissue, a motion mechanism coupled to the ultrasound transducer; a position sensor, and a communication interface.

The motion mechanism can be configured to scan the ultrasound transducer in of a linear pattern or a two-dimensional pattern. The position sensor can be configured to communicate a position of the housing and a speed of movement of the housing. The communication interface configured for wireless communication. The communication interface communicates with the ultrasound transducer, the motion mechanism, and the position sensor. The housing can also contain a rechargeable power supply or battery. The battery can supply power to the ultrasound transducer, the motion mechanism, the position sensor, and the communication interface.

In some embodiments, the controller communicates with the communication interface, which can be wireless. The controller can control a spatial parameter and a temporal parameter of the ultrasound transducer to emit the conformal distribution of ultrasound energy.

In some embodiments, a method of non-invasive treatment of plantar fascia can include identifying a damage location comprising a planter fascia; directing a conformal distribution of ultrasound energy to the plantar fascia at the damage location; creating a plurality of micro lesions in the plantar fascia at the damage location; initiating healing of a plurality of micro tears in the plantar fascia at the damage location; and sparing intervening tissue between the plantar fascia and a surface of a sole of a foot.

DRAWINGS

The present disclosure will become more fully understood from the detailed description and the accompanying drawings, wherein.

Figure 9:
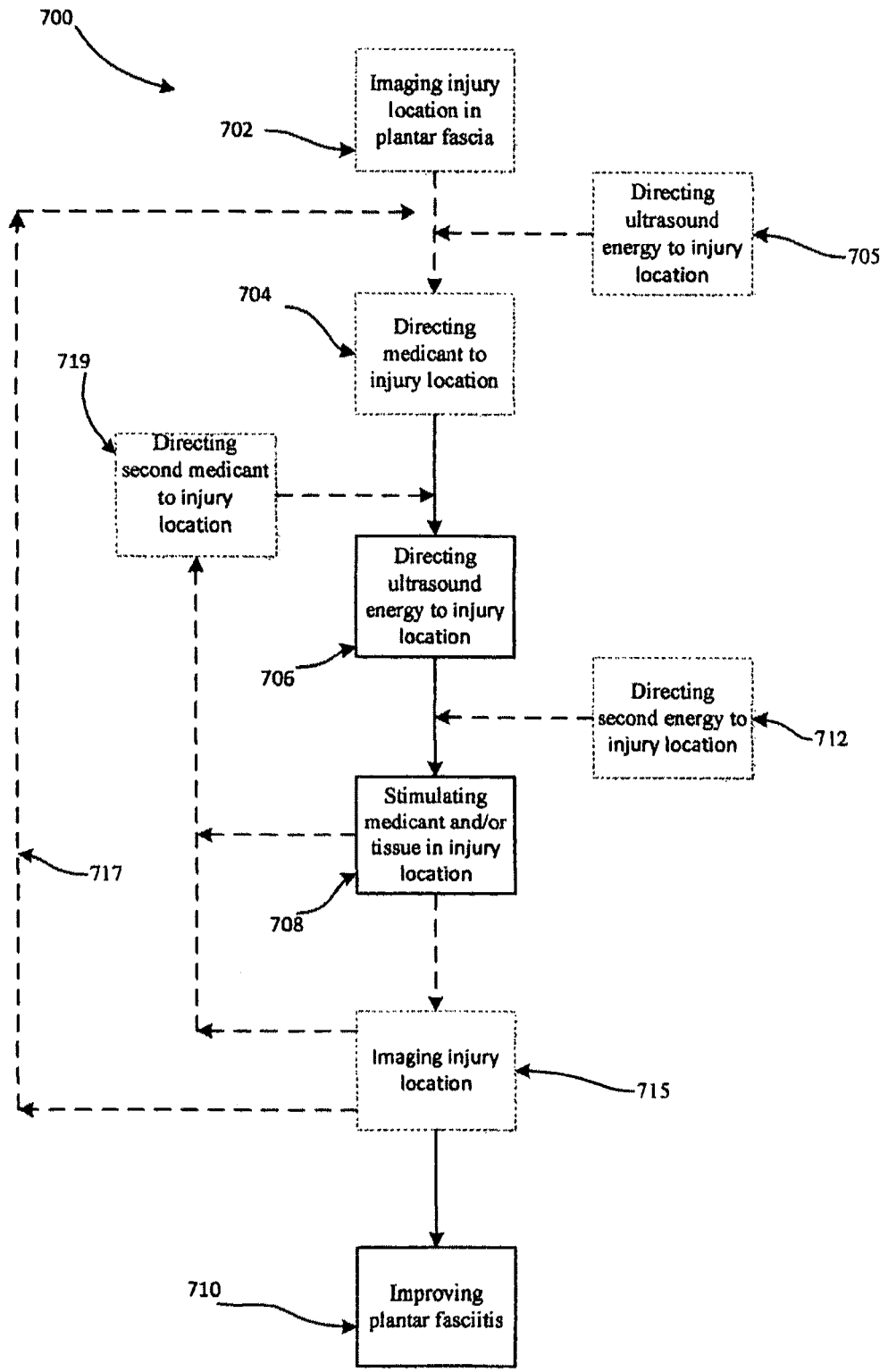

FIGS. 6 A-C illustrate various steps of a method, according to various embodiments;

FIGS. 7 A-B illustrate various steps of a method, according to various embodiments;

FIGS. 8 A-D illustrate various steps of a method, according to various embodiments; and FIG. 9 is a flow chart illustrating method, according to various embodiments.

DESCRIPTION

The following description is merely exemplary in nature and is in no way intended to limit the various embodiments, their application, or uses. As used herein, the phrase "at least one of A, B, and C" should be construed to mean a logical (A or B or C), using a non-exclusive logical or. As used herein, the phrase "A, B and/or C" should be construed to mean (A, B, and C) or alternatively (A or B or C), using a non-exclusive logical or. It should be understood that steps within a method may be executed in different order without altering the principles of the present disclosure.

The drawings described herein are for illustrative purposes only of selected embodiments and not all possible implementations, and are not intended to limit the scope of any of the various embodiments disclosed herein or any equivalents thereof. It is understood that the drawings are not drawn to scale. For purposes of clarity, the same reference numbers will be used in the drawings to identify similar elements.

The various embodiments may be described herein in terms of various functional components and processing steps. It should be appreciated that such components and steps may be realized by any number of hardware components configured to perform the specified functions. For example, various embodiments may employ various medical treatment devices, visual imaging and display devices, input terminals and the like, which may carry out a variety of functions under the control of one or more control systems or other control devices. In addition, the embodiments may be practiced in any number of medical contexts and that the various embodiments relating to a method and system for acoustic tissue treatment as described herein are merely indicative of exemplary applications for the invention. For example, the principles, features and methods discussed may be applied to any medical application.

According to various embodiments, methods and systems useful for treating plantar fascia are provided herein. The methods and systems provided herein can be noninvasive, for example, no cutting or injecting into the skin is required. Treating plantar fascia using the methods and systems provided herein minimize recovery time and may in some cases eliminate downtime for recovery. Further treating plantar fascia using the methods and systems provided herein minimize discomfort to a patient having such a procedure.

Various embodiments provide a hand-held extracorporeal system, which emits controlled ultrasound energy into layers of the skin to create a conformal region of elevated temperature in a plantar fascia. In one embodiment, a system useful for treating plantar fascia is in a handheld format which may include a rechargeable power supply.

In some embodiments, a method of treating plantar fascia can include identifying a damage location comprising a planter fascia and surrounding tissue; directing a conformal distribution of ultrasound energy to the damage location; creating a conformal region of elevated temperature in the damage location; stimulating at least one biological effect in damage location; and reducing inflammation in the surrounding tissue.

In some embodiments, the method can include imaging the damage location. In some embodiments, the method can include ablating a portion of the plantar fascia. In some embodiments, the method can include driving a medicant into the damage location. In some embodiments, the method can include peaking inflammation in the surrounding tissue and initiating a wound healing cascade in the surrounding tissue. In some embodiments, the method can include welding a portion of the plantar fascia in the damage location with the conformal ultrasound energy. In some embodiments, the method can include stimulating collagen growth in the plantar fascia. In some embodiments, the method can include creating a plurality of micro lesion in the plantar fascia and stimulating healing of a plurality of micro tears in the plantar fascia.

Some embodiments provide a system for treating plantar fascia. The system can include a hand-held probe and a controller in communication with the hand held probe. In some embodiments, the hand-held probe can include a housing, which contains an ultrasound transducer configured to focus a conformal distribution of ultrasound energy into a region of interest comprising a plantar fascia and surround subcutaneous tissue, a position sensor, and a communication interface.

In one embodiment, the system can include a motion mechanism can be configured to scan the ultrasound transducer in of a linear pattern or a two-dimensional pattern. The position sensor can be configured to communicate a position of the housing and a speed of movement of the housing. The communication interface can be wireless communication. The communication interface communicates with the ultrasound transducer, and the position sensor. The housing can also contain a rechargeable power supply or battery. The battery can supply power to the ultrasound transducer, the motion mechanism, the position sensor, and the communication interface.

In some embodiments, the controller communicates with the communication interface, which can be wireless. The controller can control a spatial parameter and a temporal parameter of the ultrasound transducer to emit the conformal distribution of ultrasound energy.

In some embodiments the controller is configured to receive the position of the housing and the speed of movement of the housing, and configured to control the timing of conformal distribution of ultrasound energy based on the position and the speed. In some embodiments, the controller is configured to control the scan of the motion mechanism based on the position and the speed.

In some embodiments of the system, the ultrasound transducer is a dual mode imaging and therapeutic ultrasound transducer configured to provide an image the region of interest and to create a conformal region of elevated temperature in the region of interest. In one embodiment, the controller comprises a display configured to display the image of the region of interest.

In some embodiments, the system can include a needle configured to transfer a medicant into the region of interest. In one embodiment, the housing contains the needle. In some embodiments, the needle can contain a medicant and in one embodiment, the medicant is contained in the housing.

In some embodiments, a method of non-invasive treatment of plantar fascia can include identifying a damage location comprising a planter fascia; directing a conformal distribution of ultrasound energy to the plantar fascia at the damage location; creating a plurality of micro lesions in the plantar fascia at the damage location; initiating healing of a plurality of micro tears in the plantar fascia at the damage location; and sparing intervening tissue between the plantar fascia and a surface of a sole of a foot.

In some embodiments, the method can include welding a portion of the plurality of micro tears in the plantar fascia at the damage location with the conformal distribution of ultrasound energy. In some embodiments, the method can include stimulating collagen growth in the plantar fascia. In some embodiments, the method can include increasing blood perfusion to the damage location.

In some embodiments, the method can include directing a second and a different conformal distribution of ultrasound energy to the plantar fascia at the damage location and initiating a therapeutic effect on the plantar fascia. In some embodiments, the method can include creating a three dimensional matrix of micro lesion in the plantar fascia at the damage location.

Figure 1:
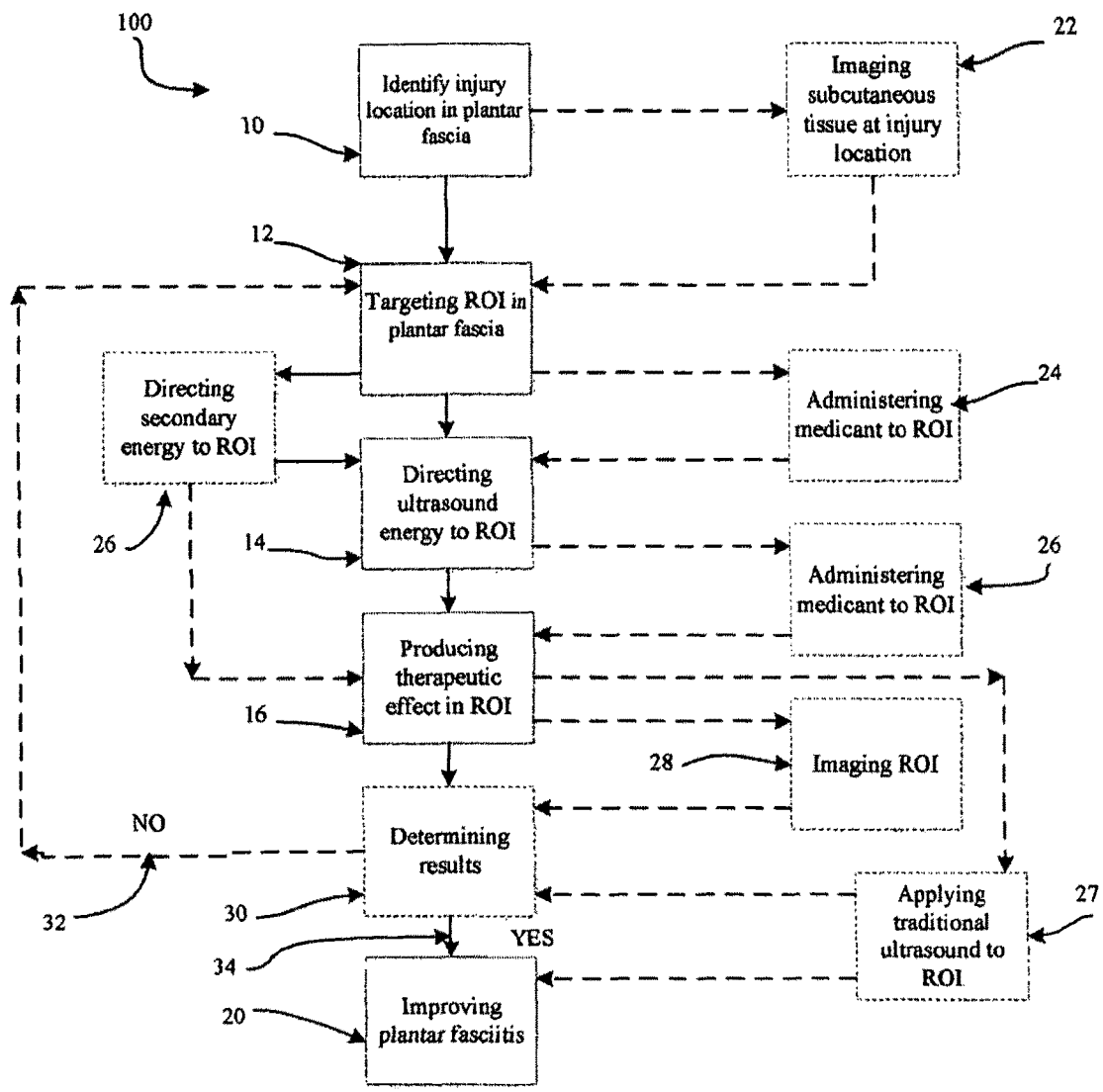
FIG. 1 is a flow chart illustrating methods of treating plantar fascia, according to various embodiments.

With reference to FIG. 1, a method of treating plantar fascia 100 is illustrated according to various embodiments. In one embodiment, the method can be used for treating plantar fasciitis. In one embodiment, the method can be used for treating plantar fasciitis. Step 10 is identifying damage location in the foot, which can be located in or near the plantar fascia of the foot. Next, Step 12 is targeting a region of interest ("ROI"). ROI can be located in subcutaneous tissue below the targeted skin surface of the foot and typically can be located below the skin surface of the sole of the foot. The subcutaneous tissue can comprise any or all of the following tissues: an epidermal layer, a dermal layer, a fat layer, a SMAS layer, a muscle layer, and a portion of the plantar fascia. In various embodiments, ROI comprises at least a portion of the plantar fascia. In some embodiments, the ROI comprises at least a portion of the plantar fascia and a portion of muscle connected thereto. In one embodiment, ROI includes a portion of the plantar fascia and surrounding tissue. Optionally, step 22 is imaging subcutaneous tissue, and more particularly the plantar fascia, below the targeted skin surface can be between steps 10 and 12 or can be substantially simultaneous with or be part of step 12.

After step 12, in some embodiments, step 14 is directing ultrasound energy to ROI. The ultrasound energy may be focused, defocused, or unfocused. The ultrasound sound energy can be weakly focused. The ultrasound energy can be directed to the subcutaneous tissue, and more particularly the plantar fascia, below the targeted skin surface.

After step 12, in some embodiments, step 14 is directing therapeutic ultrasound energy to ROI. The therapeutic ultrasound energy may be focused or unfocused. The therapeutic ultrasound energy can be focused to a portion of the plantar fascia. The therapeutic ultrasound energy may ablate a portion of a portion of the plantar fascia. The therapeutic ultrasound energy may coagulate a portion of the plantar fascia. The therapeutic ultrasound energy can produce at least one lesion in a portion of the plantar fascia. The therapeutic ultrasound energy may micro-score a portion of a portion of the plantar fascia.

The ultrasound energy may be streaming. The ultrasound energy may be directed to a first depth and then directed to a second depth. The ultrasound energy may force a pressure gradient in the subcutaneous tissue, and more particularly the plantar fascia, below the targeted skin surface. The ultrasound energy may be a first ultrasound energy effect, which comprises an ablative or a hemostatic effect, and a second ultrasound energy effect, which comprises at least one of non-thermal streaming, hydrodynamic, diathermic, and resonance induced tissue effects. Directing ultrasound energy to ROI is a non-invasive technique. As such, the targeted skin surface and the subcutaneous layers above plantar fascia are spared from injury. Such treatment does not require an incision in order to reach the plantar fascia below the targeted skin surface to enhance the targeted skin surface.

In various embodiments, a temperature of tissue receiving the ultrasound energy can be in a range from 30° C. to about 100° C., or from 43° C. to about 60° C., or from 50° C. to about 70° C., or from 30° C. to about 50° C., or from 43° C. to about 100° C., or from 33° C. to about 100° C., or from 30° C. to about 65° C., or from 33° C. to about 70° C., as well as variations thereof. Alternatively, the targeted skin surface and the layers above a target point in the subcutaneous layer are heated to a 10° C. to 15° C. above the tissue's natural state.

In various embodiments, the ultrasound energy level is in a range of about 0.1° joules to about 500 joules in order to create an ablative lesion. However, the ultrasound energy 108 level can be in a range of from about 0.1 joules to about 100 joules, or from about 1 joules to about 50 joules, or from about 0.1 joules to about 10 joules, or from about 50 joules to about 100 joules, or from about 100 joules to about 500 joules, or from about 50 joules to about 250 joules.

Further, the amount of time ultrasound energy is applied at these levels to create a lesion varies in the range from approximately 1 millisecond to several minutes. However, a range can be from about 1 millisecond to about 5 minutes, or from about 1 millisecond to about 1 minute, or from about 1 millisecond to about 30 seconds, or from about 1 millisecond to about 10 seconds, or from about 1 millisecond to about 0.1 second, or from about 1 millisecond to about 0.1 seconds, or about 0.1 seconds to about 10 seconds, or about 0.1 seconds to about 1 second, or from about 1 millisecond to about 200 milliseconds, or from about 1 millisecond to about 0.5 seconds.

The frequency of the ultrasound energy can be in a range from about 0.1 MHz to about 30 MHz, or from about 10 MHz to about 30 MHz, or from about 0.1 MHz to about 20 MHz, or from about 1 MHz to about 20 MHz, or from about 20 MHz to about 30 MHz. In some embodiments, the frequency of the ultrasound energy can be in a range from about 1 MHz to about 12 MHz, or from about 5 MHz to about 15 MHz, or from about 2 MHz to about 12 MHz or from about 3 MHz to about 7 MHz.

In some embodiments, the ultrasound energy can be emitted to depths at or below a skin surface in a range from about 0 mm to about 30 mm, or from about 0 mm to about 20 mm, or from about 0 mm to about 10 mm, or from about 0 mm to about 5 mm. In some embodiments, the ultrasound energy can be emitted to depths below a skin surface in a range from about 5 mm to about 30 mm, or from about 5 mm to about 20 mm, or from about 5 mm to about 10 mm. In some embodiments, the ultrasound energy can be emitted to depths below a skin surface in a range from about 10 mm to about 30 mm, or from about 10 mm to about 20 mm, or from about 0 mm to about 10 mm. In some embodiments, the ultrasound energy can be emitted to depths at or below a skin surface in a range from about 10 mm to about 30 mm, or from about 5 mm to about 30 mm, or from about 1 mm to about 30 mm, or from about 0 mm to about 30 mm.

In various embodiments, the ultrasound energy may be emitted at various energy levels, such as for example, the energy levels described herein. Further, the amount of time ultrasound energy is applied at these levels for various time ranges, such as for example, the ranges of time described herein. The frequency of the ultrasound energy is in various frequency ranges, such as for example, the frequency ranges described herein. The ultrasound energy can be emitted to various depths below a targeted skin surface, such as for example, the depths described herein.

Optionally, step 24, which is administering a medicant to ROI, can be between steps 12 and 14. The medicant can be any chemical or naturally occurring substance that can assist in cosmetic enhancement. For example the medicant can be but not limited to a pharmaceutical, a drug, a medication, a nutriceutical, an herb, a vitamin, a cosmetic, an amino acid, a collagen derivative, a holistic mixture, and combinations thereof.

The medicant can be administered by applying it to the skin above ROI. The medicant can be administered to the circulatory system. For example, the medicant can be in the blood stream and can be activated or moved to ROI by the ultrasound energy. The medicant can be administered by injection into or near ROI. Any naturally occurring proteins, stem cells, growth factors and the like can be used as medicant in accordance to various embodiments. A medicant can be mixed in a coupling gel or can be used as a coupling gel.

Step 16 is producing a therapeutic effect in ROI. A therapeutic effect can be cauterizing and repairing a portion of the plantar fascia. A therapeutic effect can be stimulating or increase an amount of heat shock proteins. Such a therapeutic effect can cause white blood cells to promote healing of a portion of the plantar fascia in ROI. A therapeutic effect can be peaking inflammation in a portion of ROI to decrease pain at the damage location. A therapeutic effect can be creating lesion to restart or increase the wound healing cascade at the damage location. A therapeutic effect can be increasing the blood perfusion to the damage location. Such a therapeutic effect would not require ablative ultrasound energy. A therapeutic effect can be encouraging collagen growth. A therapeutic effect can be relieving pain. A therapeutic effect may increase the "wound healing" response through the liberation of cytokines and may produce reactive changes within the tendon and muscle itself, helping to limit surrounding tissue edema and decrease an inflammatory response to an injury to the plantar fascia.

A therapeutic effect can be synergetic with the medicant administered to ROI in steps 24 and/or 26. A therapeutic effect may be an enhanced delivery of a medicant administered to ROI in steps 24 and/or 26. A therapeutic effect may increase an amount of a medicant administered to ROI in steps 24 and/or 26. A therapeutic effect may be stimulation of a medicant administered to ROI in steps 24 and/or 26. A therapeutic effect may be initiation of a medicant administered to ROI in steps 24 and/or 26. A therapeutic effect may be penetration of a medicant administered to ROI in steps 24 and/or 26.

A therapeutic effect can be healing an injury to the plantar fascia. A therapeutic effect can be repairing a tendon. A therapeutic effect can be repairing a ligament. A therapeutic effect can be repairing a muscle and a tendon connected to the muscle. Therapeutic effects can be combined.

A therapeutic effect can be produced by a biological effect that initiated or stimulated by the ultrasound energy. A biological effect can be stimulating or increase an amount of heat shock proteins. Such a biological effect can cause white blood cells to promote healing of a portion of the plantar fascia in ROI. A biological effect can be to restart or increase the wound healing cascade at the damage location. A biological effect can be increasing the blood perfusion to the damage location. A biological effect can be encouraging collagen growth at the damage location. A biological effect may increase the liberation of cytokines and may produce reactive changes within the plantar fascia. A biological effect may by peaking inflammation in the plantar fascia. A biological effect may at least partially shrinking collagen portion of the plantar fascia. A biological effect may be denaturing of proteins in ROI.

A biological effect may be creating immediate or delayed cell death (apoptosis) in the damage location. A biological effect may be collagen remodeling in the damage location. A biological effect may be the disruption or modification of biochemical cascades in the damage location. A biological effect may be the production of new collagen in the damage location. A biological effect may a stimulation of cell growth in the damage location. A biological effect may be angiogenesis in the damage location. A biological effect may a cell permeability response in the damage location. A biological effect may be an enhanced delivery of a medicant to the damage location. A biological effect may increase an amount of a medicant in the damage location. A biological effect may be stimulation of a medicant in the damage location. A biological effect may be initiation of a medicant in the damage location. A biological effect may be potentiation of a medicant in the damage location.

Optionally, step 26, which is administering medicant to ROI, can be between steps 14 and 16 or can be substantially simultaneous with or be part of step 16. The medicant useful in step 26 are essentially the same as those discussed for step 24.

In various embodiments, ultrasound energy is deposited, which can stimulate a change in at least one of concentration and activity in the damage location of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor necrosis factor-alpha (TNF-α), Vascular endothelial growth factor (VEGF), Wnt Signaling Pathway, placental growth factor (PlGF), [(Foetal Bovine Somatotrophin)] (FBS), IL-1—Cofactor for IL-3 and IL-6, which can activate T cells, IL-2—T-cell growth factor, which can stimulate IL-1 synthesis and can activate B-cells and NK cells, IL-3, which can stimulate production of all non-lymphoid cells, IL-4—Growth factor for activating B cells, resting T cells, and mast cells, IL-5, which can induce differentiation of activated B cells and eosinophils, IL-6, which can stimulate Ig synthesis and growth factor for plasma cells, IL-7 growth factor for pre-B cells, and/or any other growth factor not listed herein, and combinations thereof.

Further, medicants, as described above, can include a drug, a medicine, or a protein, and combinations thereof. Medicants can also include adsorbent chemicals, such as zeolites, and other hemostatic agents are used in sealing severe injuries quickly. Thrombin and fibrin glue are used surgically to treat bleeding and to thrombose aneurysms. Medicants can include Desmopressin is used to improve platelet function by activating arginine vasopressin receptor 1A. Medicants can include coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicants can include tranexamic acid and aminocaproic acid, can inhibit fibrinolysis, and lead to a de facto reduced bleeding rate. In addition, medicants can include steroids like the glucocorticoid cortisol.

Optionally, after step 12, step 25, which is directing secondary energy to ROI can be substantially simultaneous with or be part of step 16. However, step 25 can be administered at least one of before and after step 16. Step 25 can be alternated with step 16, which can create a pulse of two different energy emissions to ROI. Secondary energy can be provided by a laser source, or an intense pulsed light source, or a light emitting diode, or a radio frequency, or a plasma source, or a magnetic resonance source, or a mechanical energy source, or any other photon-based energy source. Secondary energy can be provided by any appropriate energy source now known or created in the future. More than one secondary energy source may be used for step 25.

Furthermore, various embodiments provide energy, which may be a first energy and a second energy. For example, a first energy may be followed by a second energy, either immediately or after a delay period. In another example, a first energy and a second energy can be delivered simultaneously. In one embodiment, the first energy and the second energy is ultrasound energy. In some embodiments, the first energy is ultrasound and the second energy is generated by one of a laser, an intense pulsed light, a light emitting diode, a radiofrequency generator, photon-based energy source, plasma source, a magnetic resonance source, or a mechanical energy source, such as for example, pressure, either positive or negative. In other embodiments, energy may be a first energy, a second energy, and a third energy, emitted simultaneously or with a time delay or a combination thereof. In one embodiment, energy may be a first energy, a second energy, a third energy, and an nth energy, emitted simultaneously or with a time delay or a combination thereof. Any of the a first energy, a second energy, a third energy, and a nth nay be generated by at least one of a laser, an intense pulsed light, a light emitting diode, a radiofrequency generator, an acoustic source, photon-based energy source, plasma source, a magnetic resonance source, and/or a mechanical energy source.

Step 20 is improving a damaged plantar fascia. Optionally, between steps 16 and 20 is step 30, which is determining results. Between steps 16 and 30 is option step 28, which is imaging ROI. The images of ROI from step 28 can be useful for the determining results of step 30. If the results of step 30 are acceptable within the parameters of the treatment then direction 34 is followed to step 20. If the results of step 30 are not acceptable within the parameters of the treatment then No direction 32 is followed back to step 12. After step 16, optionally traditional ultrasound heating can be applied to ROI in step 27. This application of traditional ultrasound heating to ROI can be useful in keeping a medicant active or providing heat to support blood perfusion to ROI after step 16. Further examples and variations of treatment method 100 are discussed herein.

In addition, various different subcutaneous tissues, including for example, the plantar fascia and surrounding tissue, may be treated by method 100 to produce different bio-effects, according to some embodiments of the present disclosure. Furthermore, any portion of the plantar fascia may be treated by method 100 to produce one or more bio-effects, as described herein, in accordance to various embodiments. In order to treat a specific damage location and to achieve a desired bio-effect, therapeutic ultrasound energy may be directed to a specific depth within ROI to reach the targeted subcutaneous tissue, such as, for example, plantar fascia. For example, if it is desired to cut a portion of the plantar fascia by applying therapeutic ultrasound energy 120 at ablative levels, which may be approximately 5 mm to 15 mm below skin surface or at other depths as described herein. An example of ablating the plantar fascia can include a series of lesions ablated into the plantar fascia. Besides ablating a portion of the plantar fascia, other bio-effects may comprise incapacitating, partially incapacitating, severing, rejuvenating, removing, ablating, micro-ablating, shortening, manipulating, or removing tissue either instantly or over time, and combinations thereof.

Depending at least in part upon the desired bio-effect and the subcutaneous tissue being treated, method 100 may be used with an extracorporeal, non-invasive procedure. Also, depending at least in part upon the specific bio-effect and tissue targeted, temperature may increase within ROI may range from approximately 30° C. to about 60° C., or in a range from about 30° C. to about 100° C., or in other appropriate temperature ranges that are described herein.

Depending at least in part upon the desired bio-effect and the plantar fascia and surrounding tissue, being treated, method 100 may be used with an extracorporeal, non-invasive procedure. Also, depending at least in part upon the specific bio-effect and tissue targeted, temperature may increase within ROI may range from approximately 10° C. to about 15° C.

Other bio-effects to target tissue, such as, the plantar fascia and surrounding tissue, can include heating, cavitation, steaming, or vibro-accoustic stimulation, and combinations thereof. In various embodiments, therapeutic ultrasound energy is deposited in a matrices of micro-coagulative zones to an already injured plantar fascia can increase the "wound healing" response through the liberation of cytokines and may produce reactive changes within the plantar fascia itself, helping to limit surrounding tissue edema and decrease the inflammatory response to an injury to plantar fascia. In various embodiments, therapeutic ultrasound energy is deposited in a matrices of micro-coagulative zones to an already injured plantar fascia changes at least one of concentration and activity of inflammatory mediators (such as but not limited to TNF-A, IL-1) as well as growth factors (such as but not limited to TGF-B1, TGF-B3) at the site of the injured plantar fascia.

In various embodiments, therapeutic ultrasound energy is deposited in a matrices of micro-coagulative zones to an already plantar fascia, which can stimulate a change in at least one of concentration and activity of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumour necrosis factor-alpha (TNF-α), Vascular endothelial growth factor (VEGF), Wnt Signaling Pathway, placental growth factor (PlGF), [(Foetal Bovine Somatotrophin)] (FBS), IL-1—Cofactor for IL-3 and IL-6, which can activate T cells, IL-2—T-cell growth factor, which can stimulate IL-1 synthesis and can activate B-cells and NK cells, IL-3, which can stimulate production of all non-lymphoid cells, IL-4—Growth factor for activating B cells, resting T cells, and mast cells, IL-5, which can induce differentiation of activated B cells and eosinophils, IL-6, which can stimulate Ig synthesis and growth factor for plasma cells, IL-7 growth factor for pre-B cells, and/or any other growth factor not listed herein, and combinations thereof.

Further, medicants, as described above, can include a drug, a medicine, or a protein, and combinations thereof. Medicants can also include adsorbent chemicals, such as zeolites, and other hemostatic agents are used in sealing severe injuries quickly. Thrombin and fibrin glue are used surgically to treat bleeding and to thrombose aneurysms. Medicants can include Desmopressin is used to improve platelet function by activating arginine vasopressin receptor 1A. Medicants can include coagulation factor concentrates are used to treat hemophilia, to reverse the effects of anticoagulants, and to treat bleeding in patients with impaired coagulation factor synthesis or increased consumption. Prothrombin complex concentrate, cryoprecipitate and fresh frozen plasma are commonly-used coagulation factor products. Recombinant activated human factor VII can be used in the treatment of major bleeding. Medicants can include tranexamic acid and aminocaproic acid, can inhibit fibrinolysis, and lead to a de facto reduced bleeding rate. In addition, medicant can include steroids, (anabolic steroids and/or costisol steroids), for example glucocorticoid cortisol or prednisone. Medicant can include compounds as alpha lipoic acid, DMAE, vitamin C ester, tocotrienols, and phospholipids. Medicant can be Medicant can be a pharmaceutical compound such as for example, cortisone, Etanercept, Abatacept, Adalimumab, or Infliximab. Medicant can include platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue. Medicant can be a prothrombin complex concentrate, cryoprecipitate and fresh frozen plasma, which are commonly-used coagulation factor products. Medicant can be a recombinant activated human factor VII, which can be used in the treatment of major bleeding. Medicant can include tranexamic acid and aminocaproic acid, can inhibit fibrinolysis, and lead to a de facto reduced bleeding rate. In some embodiments, medicant can be Botox.

According to various embodiments of method 100, ultrasound probe is coupled directly to ROI, as opposed to skin surface, to treat a portion of the plantar fascia. For example, ultrasound probe can be integrated to or attached to a tool, such as, for example, an arthroscopic tool, laparoscopic tool, or an endoscopic tool that may be inserted into a patient's body with minimal invasiveness.

In various embodiments, method 100 can treat either recent or older injuries, or combinations thereof. Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. In various embodiments, method 100 can treat chronic inflammation. In various embodiments, method 100 can treat acute inflammation. In some embodiments, method 100 can treat a combination of acute and chronic inflammation.

Figure 2:
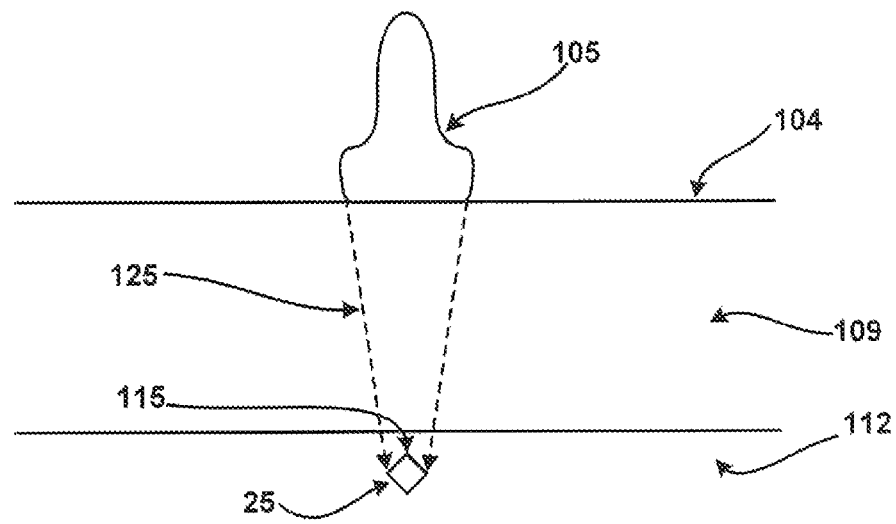
FIG. 2 is a cross sectional view illustrating ultrasound energy directed to a plantar fascia layer, according to various embodiments.

Now moving to FIG. 2, a cross sectional view of tissue layers and ultrasound energy directed to a fibrous tissue layer comprising a portion of the plantar fascia 112, according to various embodiments, is illustrated. Typically, ultrasound energy propagates as a wave with relatively little scattering, over depths up to many centimeters in tissue depending on the ultrasound frequency. The focal spot size achievable with any propagating wave energy, depends on wavelength. Ultrasound wavelength is equal to the acoustic velocity divided by the ultrasound frequency. Attenuation (absorption, mainly) of ultrasound by tissue also depends on frequency.

In various embodiments, ultrasound energy 120 creates a conformal region of elevated temperature 25. In some embodiments, conformal region of elevated temperature 25 is a conformal energy deposition, which increases the temperature in a conformal region of tissue in ROI 115 by about 5° C. to 65° C. above the internal body temperature or higher. In some embodiments, conformal region of elevated temperature 25 is a conformal energy deposition, which is placed at a selected depth in the tissue in ROI 115 and has a defined shape and volume. In some embodiments, conformal region of elevated temperature 25 is a shaped conformal distribution of elevated temperature in ROI 115, which can be created through adjustment of the strength, depth, and type of focusing, energy levels and timing cadence.

In various embodiment, ultrasound probe 105 is configured with the ability to controllably produce conformal distribution of elevated temperature in soft tissue within ROI 115 through precise spatial and temporal control of acoustic energy deposition, i.e., control of ultrasound probe 105 is confined within selected time and space parameters, with such control being independent of the tissue. The ultrasound energy 120 can be controlled to produce a conformal distribution of elevated temperature in soft tissue within ROI 115 using spatial parameters. The ultrasound energy 120 can be controlled to produce conformal distribution of elevated temperature in soft tissue within ROI 115 using temporal parameters. The ultrasound energy 120 can be controlled to produce a conformal distribution of elevated temperature in soft tissue within ROI 115 using a combination of spatial parameters and temporal parameters. In some embodiments, a conformal distribution of elevated temperature in soft tissue within ROI 115 is conformal region of elevated temperature 25 in ROI 115.

In various embodiments, conformal region of elevated temperature 25 can create a lesion in ROI 115. In various embodiments, conformal region of elevated temperature 25 can initiate thermal injury in a portion of ROI 115. In various embodiments, conformal region of elevated temperature 25 can initiate or stimulate coagulation in a portion of ROI 115. In various embodiments, conformal region of elevated temperature 25 can be one of a series of micro scoring in ROI 115. In various embodiments, conformal region of elevated temperature 25 can with a first ultrasound energy deposition and a second energy deposition. In one embodiment, second energy deposition is ultrasound energy. In some embodiments, second energy is any one of second energy that may be used for method 100, as discussed herein.

In various embodiments, conformal region of elevated temperature 25 can stimulate and/or initiate a therapeutic effect. In various embodiments, conformal region of elevated temperature 25 can stimulate and/or initiate a biological effect. In various embodiments, conformal region of elevated temperature 25 can denature tissue in ROI 115. In various embodiments, conformal region of elevated temperature 25 can drive a medicant into ROI 115. In various embodiments, conformal region of elevated temperature 25 can activate a medicant in ROI 115. In various embodiments, conformal region of elevated temperature 25 can create immediate or delayed cell death (apoptosis) in the ROI. In various embodiments, conformal region of elevated temperature 25 can create one or more ablation zones in ROI 115. In various embodiments, conformal region of elevated temperature 25 can increase blood perfusion in ROI 115.

In one embodiment, conformal region of elevated temperature 25 can be created by heating a portion of ROI 115 with ultrasound energy 120. In one embodiment, conformal region of elevated temperature 25 can be created by cavitation in ROI 115, which is initiated by ultrasound energy 120. In one embodiment, conformal region of elevated temperature 25 can be created by streaming ultrasound energy 120 into ROI 115. In one embodiment, conformal region of elevated temperature 25 can be created by vibro-accoustic stimulation in ROI 115, which is initiated by ultrasound energy 120. In one embodiment, conformal region of elevated temperature 25 can be created by a combination of two or more of heating, cavitation, streaming, or vibro-accoustic stimulation.

In some embodiments, conformal region of elevated temperature 25 can be a shaped lesion, which can be created through adjustment of the strength, depth, and type of focusing, energy levels and timing cadence. For example, focused ultrasound energy 120 can be used to create precise arrays of microscopic thermal ablation zones. Ultrasound energy 120 can produce an array of ablation zones deep into the layers of the soft tissue. Detection of changes in the reflection of ultrasound energy can be used for feedback control to detect a desired effect on the tissue and used to control the exposure intensity, time, and/or position. In various embodiments, ultrasound probe 105 is configured with the ability to controllably produce conformal region of elevated temperature 25 in soft tissue within ROI 115 through precise spatial and temporal control of acoustic energy deposition, i.e., control of ultrasound probe 105 is confined within selected time and space parameters, with such control being independent of the tissue.

In accordance with various embodiments, ultrasound probe 105 can be configured for spatial control of ultrasound energy 120 by controlling the manner of distribution of the ultrasound energy 120 to create conformal region of elevated temperature 25. For example, spatial control may be realized through selection of the type of one or more spatial parameters of the transducer configurations insonifying ROI 115, selection of the placement and location of ultrasound probe 105 for delivery of ultrasound energy 120 relative to ROI 115 e.g., ultrasound probe 105 being configured for scanning over part or whole of ROI 115 to produce a contiguous conformal region of elevated temperature 25 having a particular orientation or otherwise change in distance from ROI 115, and/or control of other environment parameters, e.g., the temperature at the acoustic coupling interface can be controlled, and/or the coupling of ultrasound probe 105 to tissue. Other spatial control can include but are not limited to geometry configuration of ultrasound probe 105 or transducer assembly, lens, variable focusing devices, variable focusing lens, stand-offs, movement of ultrasound probe, in any of six degrees of motion, transducer backing, matching layers, number of transduction elements in transducer, number of electrodes, or combinations thereof.

In various embodiments, ultrasound probe 105 can also be configured for temporal control of ultrasound energy 120 by controlling the timing of the distribution of the ultrasound energy 120 to create conformal region of elevated temperature 25. For example, temporal control may be realized through adjustment and optimization of one or more temporal parameters, such as for example, drive amplitude levels, frequency, waveform selections, e.g., the types of pulses, bursts or continuous waveforms, and timing sequences and other energy drive characteristics to control thermal ablation of tissue. Other temporal parameters can include but are not limited to full power burst of energy, shape of burst, timing of energy bursts, such as, pulse rate duration, continuous, delays, etc., change of frequency of burst, burst amplitude, phase, apodization, energy level, or combinations thereof.

The spatial and/or temporal control can also be facilitated through open-loop and closed-loop feedback arrangements, such as through the monitoring of various spatial and temporal characteristics. As a result, control of acoustical energy within six degrees of freedom, e.g., spatially within the X, Y and Z domain, as well as the axis of rotation within the XY, YZ and XZ domains, can be suitably achieved to generate conformal region of elevated temperature 25 of variable shape, size and orientation. For example, through such spatial and/or temporal control, ultrasound probe 105 can enable the regions of thermal injury to possess arbitrary shape and size and allow the tissue to be destroyed (ablated) in a controlled manner.

The tissue layers illustrated in FIG. 2 are subcutaneous layer 109 and fibrous soft tissue layer comprising a portion of plantar fascia 112. Ultrasound probe 105 emits ultrasound energy 120 in ROI 115. In various embodiments, ultrasound probe 105 is capable of emitting ultrasound energy 120 at variable depths in ROI 115, such as, for example, the depths described herein. Ultrasound probe 105 is capable of emitting ultrasound energy 120 as a single frequency, variable frequencies, or a plurality of frequencies, such as, for example, the frequency ranges described herein. Ultrasound probe 105 is capable of emitting therapeutic ultrasound energy 120 for variable time periods or to pulse the emission over time, such as, for example, those time intervals described herein. Ultrasound probe 105 is capable of providing various energy levels of ultrasound energy 120, such as, for example, the energy levels described herein. Ultrasound probe 105 may be individual hand-held device, or may be part of a treatment system. The ultrasound probe 105 can provide both therapeutic ultrasound energy 120 and imaging ultrasound energy. However, ultrasound probe 105 may provide only therapeutic ultrasound energy 120. Ultrasound probe 105 may comprise a therapeutic transducer and a separate imaging transducer. Ultrasound probe 105 may comprise a transducer or a transducer array capable of both therapeutic and imaging applications. According to an alternative embodiment, ultrasound probe 105 is coupled directly to plantar fascia 112, as opposed to skin surface 104 to treat a portion of plantar fascia 112. For example, ultrasound probe 105 can be integrated to or attached to a tool, such as, for example, an arthroscopic tool, laparoscopic tool, or an endoscopic tool that may be inserted into a patient's body with minimal invasiveness.

Figure 3:
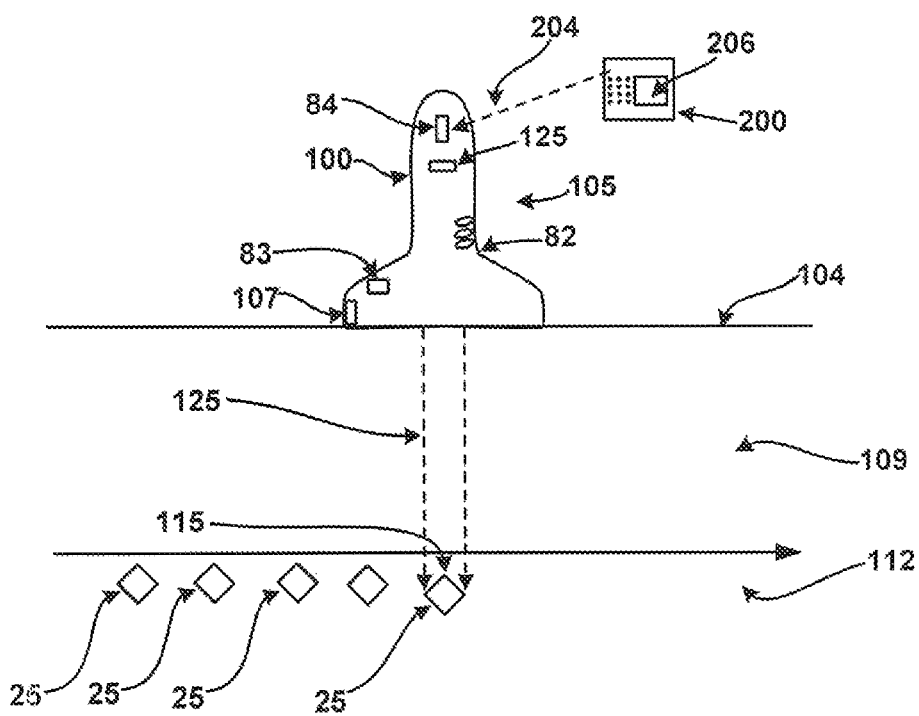
FIG. 3 is a cross sectional view illustrating ultrasound energy directed to a plantar fascia layer, according to various embodiments.

Referring to FIG. 3, a cross sectional view of ultrasound energy 120 creating a plurality of conformal regions of elevated temperature 25 in fibrous soft tissue layer comprising a portion of plantar fascia 112 is illustrated. In some embodiments, ROI 115 comprises a plantar fascia 112. In some embodiments, ROI 115 can comprise skin surface 104, subcutaneous tissue 109, and plantar fascia 112. In some embodiments, ultrasound probe 105 images at least a portion of one of skin surface 104, subcutaneous tissue 109, and plantar fascia 112. In one embodiment, ultrasound probe 105 images at least a portion of plantar fascia 112. Ultrasound probe 105 emits ultrasound energy 120 to at least a portion of plantar fascia 112. In various embodiments, ultrasound energy 120 treats a portion of plantar fascia 112. In various embodiments, ultrasound probe 105 may be used for method 100. In various embodiments, method 100 can be implemented using any or all of the elements illustrated in FIG. 3.

As will be appreciated by those skilled in the art, at least a portion of method 100 or a variation of method 100 can be implemented using any or all of the elements illustrated in FIG. 3.

With further reference to FIG. 3 and according to one embodiment, a hand held ultrasound probe 115 is illustrated. In various embodiments, ultrasound transducer 105 comprises transducer 125, as described herein, and may be controlled and operated by a hand-held format control system. An external battery charger can be used with rechargeable-type batteries 84 or the batteries 84 can be single-use disposable types, such as M-sized cells. Power converters produce voltages for powering a driver/feedback circuit with tuning network driving transducer 125. Ultrasound probe 105 is coupled to skin surface 104 via one or more tip, which can be composed of at least one of a solid media, semi-solid e.g. gelatinous media, and/or liquid media equivalent to an acoustic coupling agent, which can be contained within a housing. Tip is coupled to skin surface 104 with an acoustic coupling agent. In addition, a microcontroller and timing circuits with associated software and algorithms provide control and user interfacing via a display or LED-type indicators 83, and other input/output controls 82, such as switches and audio devices. A storage element, such as an Electrically Erasable Programmable Read-Only Memory ("EEPROM"), secure EEPROM, tamper-proof EEPROM, or similar device can hold calibration and usage data. A motion mechanism with feedback can be controlled to scan the transducer 125 in a linear pattern or a two-dimensional pattern or over a varied depth. Other feedback controls comprise capacitive, acoustic, or other coupling detection means, limiting controls, and thermal sensor. EEPROM can be coupled with at least one of tip, transducer 125, thermal sensor, coupling detector, and tuning network. Data for EEPROM can be collected in a controller and connected to treatment data.

Ultrasound transducer 125 can comprise tip that can be disposed of after contacting a patient and then replaced for sanitary reasons. In an exemplary embodiment, tip is disposable, and for example EEPROM determines if tip has been used and will not allow treatment to begin tip that has been previously used. In some embodiments, tip has height which can control therapeutic ultrasound energy 120 depth into ROI 115. In some embodiments, a plurality of tips, each having a different height may be used to direct ultrasound energy 120 to a plurality of depths in ROI 115.

Transducer 125 may further comprise a reflective surface, tip, or area at the end of the transducer 125 that emits therapeutic ultrasound energy 120. This reflective surface may enhance, magnify, or otherwise change therapeutic ultrasound energy 120 emitted from ultrasound probe 105.

In some embodiments, ultrasound probe 105 comprises imaging transducer 80. In some embodiments, ultrasound probe 105 comprises position sensor 107, as described herein. In some embodiments, transducer 125 is operable for emitting therapeutic ultrasound energy 120 and may be operable for imaging, as described herein.

In various embodiments, ultrasound probe 105 comprises transducer 125. In some embodiments, ultrasound probe 105 comprises position sensor 107, as described herein. In some embodiments, transducer 125 is a single element operable for imaging and emitting ultrasound energy 120, as described herein. In some embodiments, transducer 125 is a multi-element array operable for imaging and emitting therapeutic ultrasound energy 120, as described herein. However, in some embodiments, transducer 125 is operable for emitting therapeutic ultrasound energy 120 and is not operable for imaging, as described herein. In some embodiments, transducer 125 is a dual-mode imaging and therapeutic transducer configured to provide imaging ultrasound energy and therapeutic ultrasound energy.

In various embodiments, transducer 125, and optionally position sensor 107 can be held within enclosure. In an exemplary embodiment, enclosure is designed for comfort and control while used in an operator's hand. Enclosure may also contain various electronics, EEPROM, interface connection, motion mechanisms, and/or ram for holding programs.

In various embodiments, ultrasound probe 105 comprises enclosure containing transducer 125 and optionally position sensor 107. Ultrasound probe 105 can be coupled to targeted skin surface 104. Ultrasound energy 120 can be emitted by transducer 125 to create conformal region of elevated temperature 25. In various embodiments, weakly focused ultrasound energy 120 can create conformal region of elevated temperature 25.

In various embodiments, position sensor 107 may determine a distance 117 between pulses of therapeutic ultrasound energy 108 to create a plurality of conformal region of elevated temperature 25, which are evenly spaced or disposed in any spatial configuration in one-, two-, or three-dimensions. As ultrasound probe 105 is moved in direction 130, position sensor 107 determines distance, regardless of a speed that ultrasound probe 105 is moved, at which a pulse of ultrasound energy 120 is to be emitted in to ROI. In various embodiments ultrasound probe 105 is triggered automatically via a timer and in combination with a position sensor 107 to assure motion.

However, in various embodiments, ultrasound probe 105 comprises position sensor 107. Position sensor 107 can be integrated into ultrasound probe 105 or attached to ultrasound probe 105. In an exemplary embodiment, position sensor 107 is a motion sensor measuring position of ultrasound probe 105. Such a motion sensor can calculate distance traveled along skin surface 104. Such a motion sensor may determine a speed of movement of ultrasound probe 105 along skin surface 104 and determine if the speed is accurate for the procedure or treatment that is elected. For example if the speed is too fast, motion sensor can signal an indicator to slow the speed and/or can signal transducer 125 to stop emitting ultrasound energy 120.

In various embodiments, position sensor 107 can include a laser position sensor. For example, position sensor 107 can track position like a computer mouse that uses a laser sensor as opposed to an older version of a mouse with a roller ball. Position sensor 107 can communicate position data versus time to a display to track a position of ultrasound probe 105, such as, for example, overlaid on an image of ROI, overlaid on an image of skin surface 104, as referenced to geotagged features, as reference to targeted location, as referenced to a prior procedures, and combinations thereof. In an exemplary a treatment plan can include a movement pattern of ultrasound probe 105. Such a movement pattern can be displayed and the position sensor 107 can track a position of ultrasound probe 105 during a cosmetic procedure as compared to the movement pattern. Tracking ultrasound probe 105 with position sensor and comparing the tracked movement to a predetermined movement may be useful as a training tool. In an exemplary embodiment, laser position sensor can geotag a feature on skin surface 104.

In various embodiments, position sensor 107 may determine a distance between pulses of therapeutic ultrasound energy 108 to create a plurality of conformal regions of elevated temperature 25 which are evenly spaced or disposed in any spatial configuration in one-, two-, or three-dimensions. As ultrasound probe 105 is moved in direction 130, position sensor 107 determines distance, regardless of a speed that ultrasound probe 105 is moved, at which a pulse of therapeutic ultrasound energy 120 is to be emitted in to ROI 115. In various embodiments ultrasound probe 105 is triggered automatically via a timer and in combination with a position sensor 107 to assure motion.

Position sensor 107 may be located behind a transducer, in front of a transducer array, or integrated into a transducer array. Ultrasound probe 105 may comprise more than one position sensor 107, such as, for example, a laser position sensor and a motion sensor, or a laser position sensor and a visual device, or a motion sensor and a visual device, or a laser position sensor, a motion sensor, and a visual device. Additional embodiments of position sensor 107 may be found in U.S. Pat. No. 7,142,905, entitled "Visual Imaging System for Ultrasonic Probe" issued Nov. 28, 2006, and U.S. Pat. No. 6,540,679, entitled "Visual Imaging System for Ultrasonic Probe" issued Apr. 1, 2003, both of which are incorporated by reference.

Position sensor 107 can be integrated into ultrasound probe 105 or attached to ultrasound probe 105. In one embodiment, position sensor 107 is an optical sensor measuring 1-D, 2-D, or 3-D movement 130 of ultrasound probe 105 versus time while probe travels along skin surface 104. Such a position sensor may control conformal region of elevated temperature 25 sequence directly, by using position information in the treatment system to trigger emission of ultrasound energy 120. In various embodiments, cosmetic enhancement can be triggered when the ultrasound probe 105 reaches a fixed or pre-determined range away from the last of conformal region of elevated temperature 25. Speed of motion can be used to control therapeutic ultrasound energy 120. For example, if the motion is too fast information can be provided to the user to slow down and/or energy can be dynamically adjusted within limits. Position information may also be used to suppress energy if crossing over the same spatial position, if desired. Such a position sensor 107 may also determine if ultrasound probe 105 is coupled to skin surface 104, to safely control energy delivery and provide information to users.

In various embodiments, ultrasound probe 105 can comprise a tissue contact sensor. In one embodiment, tissue contact sensor communicates whether ultrasound probe 105 is coupled to the ROI 115. The tissue contact sensor may measure a capacity of a skin surface 104 above the ROI 115 and communicate a difference between the capacity of the contact to the skin surface 104 and the capacity of air. In one embodiment, the tissue contact sensor is initiated or turned on by pressing ultrasound probe 105 against skin surface 104.

In various embodiments, ultrasound probe 105 can be in communication with wireless device 200 via wireless interface 204. Typically, wireless device 204 has display 206 and a user interface such as, for example, a keyboard. Examples of wireless device 200 can include but are not limited to: personal data assistants ("PDA"), cell phone, Iphone® device by Apple Computer, Inc., Ipad® device by Apple Computer, Inc., computer, laptop, netbook, or any other such device now known or developed in the future. Examples of wireless interface 206 include but are not limited to any wireless interface described herein and any such wireless interface now known or developed in the future. Accordingly, ultrasound probe 105 comprises any hardware, such as, for example, electronics, antenna, and the like, as well as, any software that may be used to communicate via wireless interface 206. In various embodiments, wireless device 200 can display an image generated by handheld probe 105. In various embodiments, wireless device 200 can control handheld ultrasound probe 105. In various embodiments, wireless device 200 can store data generated by handheld ultrasound probe 105.

Therapeutic ultrasound energy 120 from transducer 125 may be spatially and/or temporally controlled at least in part by changing the spatial parameters of transducer 125, such as the placement, distance, treatment depth and transducer 125 structure, as well as by changing the temporal parameters of transducer 125, such as the frequency, drive amplitude, and timing, with such control handled via controller in hand-held assembly of ultrasound probe 105. In various embodiments, ultrasound probe 105 comprises a transducer 125 capable of emitting ultrasound energy 120 into ROI 115 to create conformal region of elevated temperature 25. This may heat ROI 115 at a specific depth to target plantar fascia 112 causing a portion of plantar fascia 112 to be ablated, micro-ablated, coagulated, incapacitated, partially incapacitated, rejuvenated, shortened, paralyzed, or removed.

In some embodiments, ultrasound probe 105 can be moved in at least one direction 114 to provide a plurality of conformal region of elevated temperature 25 in a tissue layer. In various embodiments, a plurality of conformal region of elevated temperature 25 can be placed in a pattern in at least one tissue layer, such as, for example, a 1-D pattern, a 2-D pattern, a 3-D pattern, or combinations thereof.

In one embodiment, ultrasound probe 105 comprises a single transducer element and while emitting therapeutic ultrasound energy 120 in a pulsed matter, is moved in a linear motion along skin surface 104 to create a 1-D pattern of a plurality of conformal region of elevated temperature 25 in at least one tissue layer. In one embodiment, ultrasound probe 105 comprises a linear array of transducers and while emitting therapeutic ultrasound energy 120 in a pulsed matter, is moved along the linear vector of the array on skin surface 104 to create a 1-D pattern of a plurality of conformal region of elevated temperature 25 in at least one tissue layer.

In one embodiment, ultrasound probe 105 comprises a linear array of transducers and while emitting therapeutic ultrasound energy 120 in a pulsed matter, is moved along the non-linear vector of the array on skin surface 104 to create a 2-D pattern of a plurality of conformal region of elevated temperature 25 in at least one tissue layer. In one embodiment, ultrasound probe 105 comprises an array of transducers and while emitting therapeutic ultrasound energy 120 in a pulsed matter, is moved along skin surface 104 to create a 2-D pattern of a plurality of conformal region of elevated temperature 25 in at least one tissue layer.

In one embodiment, ultrasound probe 105 comprises an array of transducers, wherein the array comprises a first portion focusing to a first depth and a second portion focusing to a second depth, and while emitting therapeutic ultrasound energy 120 in a pulsed matter, is moved along skin surface 104 to create a 3-D pattern of a plurality of conformal region of elevated temperature 25 in at least one tissue layer. In one embodiments, ultrasound probe 105 comprises at least two arrays of transducers, wherein a first array focusing to a first depth and a second array focusing to a second depth, and while each of the arrays emitting therapeutic ultrasound energy 120 in a pulsed matter, is moved along skin surface 104 to create a 3-D pattern of a plurality of conformal region of elevated temperature 25 in at least one tissue layer. In one embodiment, ultrasbund probe 105 comprises a linear array of transducers and while emitting therapeutic ultrasound energy 120 in a pulsed matter, is moved along the non-linear vector of the array on skin surface 104 focused to a first depth then moved in the same direction along skin surface focused at a second depth to create a 3-D pattern of a plurality of conformal region of elevated temperature 25 in at least one tissue layer. In one embodiment, ultrasound probe 105 comprises an array of transducers and while emitting therapeutic ultrasound energy 120 in a pulsed matter, is moved along skin surface 104 focused to a first depth then moved in the same direction along skin surface focused at a second depth to create a 3-D pattern of a plurality of conformal region of elevated temperature 25 in at least one tissue layer.

In some embodiments, ultrasound probe 105 can be moved in at least one direction 114 to create a plurality of conformal region of elevated temperature 25 in plantar fascia 112. In one embodiment, a plurality of conformal region of elevated temperature 25 in plantar fascia 112 can be a plurality of lesions in plantar fascia 112. In various embodiments, a plurality of conformal regions of elevated temperature 25 can be placed in a pattern in a portion of plantar fascia 112, such as, for example, a 1-D pattern, a 2-D pattern, a 3-D pattern, or combinations thereof.

In one embodiment, therapeutic ultrasound energy 120 ablates a portion plantar fascia 112 creating region of elevated temperature 25, which can be a lesion. In one embodiment, therapeutic ultrasound energy 120 coagulates a portion of plantar fascia 112. In some embodiments, ultrasound energy 120 can create ablation zone 150 in a tissue layer, at which a temperature of tissue is raised to at least 43° C., or is raised to a temperature in the range form about 43° C. to about 100° C., or from about 50° C. to about 90° C., or from about 55° C. to about 75° C., or from about 50° C. to about 65° C., or from about 60° C. to about 68° C.

In some embodiments, plantar fascia 112 is a tough yet flexible band of fibrous connective tissue that can connect muscle to bone. Plantar fascia can be composed of parallel arrays of collagen fibers closely packed together. The fibers are mostly collagen type I, however, both collagen type III and V may be present. Collagen molecules are produced by tenocytes and aggregate end-to-end and side-to side to produce collagen fibrils, organized fibril bundles form fibers, groups of fibers form macroaggregates, groups of macroaggregates bounded by endotendon form fascicles and groups of fascicles bounded by epitendon and peritendon can form plantar fascia 112. In some embodiments, conformal region of elevated temperature 25 in plantar fascia 112 can encourage collagen growth. In some embodiments, conformal region of elevated temperature 25 in plantar fascia 112 can initiate and/or stimulate collagen production in plantar fascia 112. In some embodiments, conformal region of elevated temperature 25 in plantar fascia 112 can increase an amount of collegan in plantar fascia 112.

In various embodiments, methods, described herein, can stimulate coagulation by depositing target ultrasound energy 120 with or without a medicant. In some embodiments, methods, described herein, can initiate wound healing cascade by depositing target ultrasound energy 120 with or without a medicant. The wound healing cascade of secondary hemostasis has two pathways which lead to fibrin formation. These are the contact activation pathway (formerly known as the intrinsic pathway), and the tissue factor pathway (formerly known as the extrinsic pathway).

In some embodiments, soon after thermal injury created by conformal region of elevated temperature 25, a wound healing cascade can be unleashed. This cascade is usually said to take place in three phases: the inflammatory, proliferative, and maturation stages. In some embodiments, methods, described herein, can peak inflammation by depositing target ultrasound energy with or without a medicant. In the inflammatory phase, macrophages and other phagocytic cells kill bacteria, debride damaged tissue and release chemical factors such as growth hormones that encourage fibroblasts, epithelial cells and endothelial cells which make new capillaries to migrate to the area and divide. In the proliferative phase, immature granulation tissue containing plump active fibroblasts forms. Fibroblasts quickly produce abundant type III collagen, which fills the defect left by an open wound. In the maturation stage, the fibroblasts produce less collagen and can mature into myofibroblasts which contain the same type of actin found in smooth muscle, which enables them to contract and reduce the size of the wound.

Figure 4:
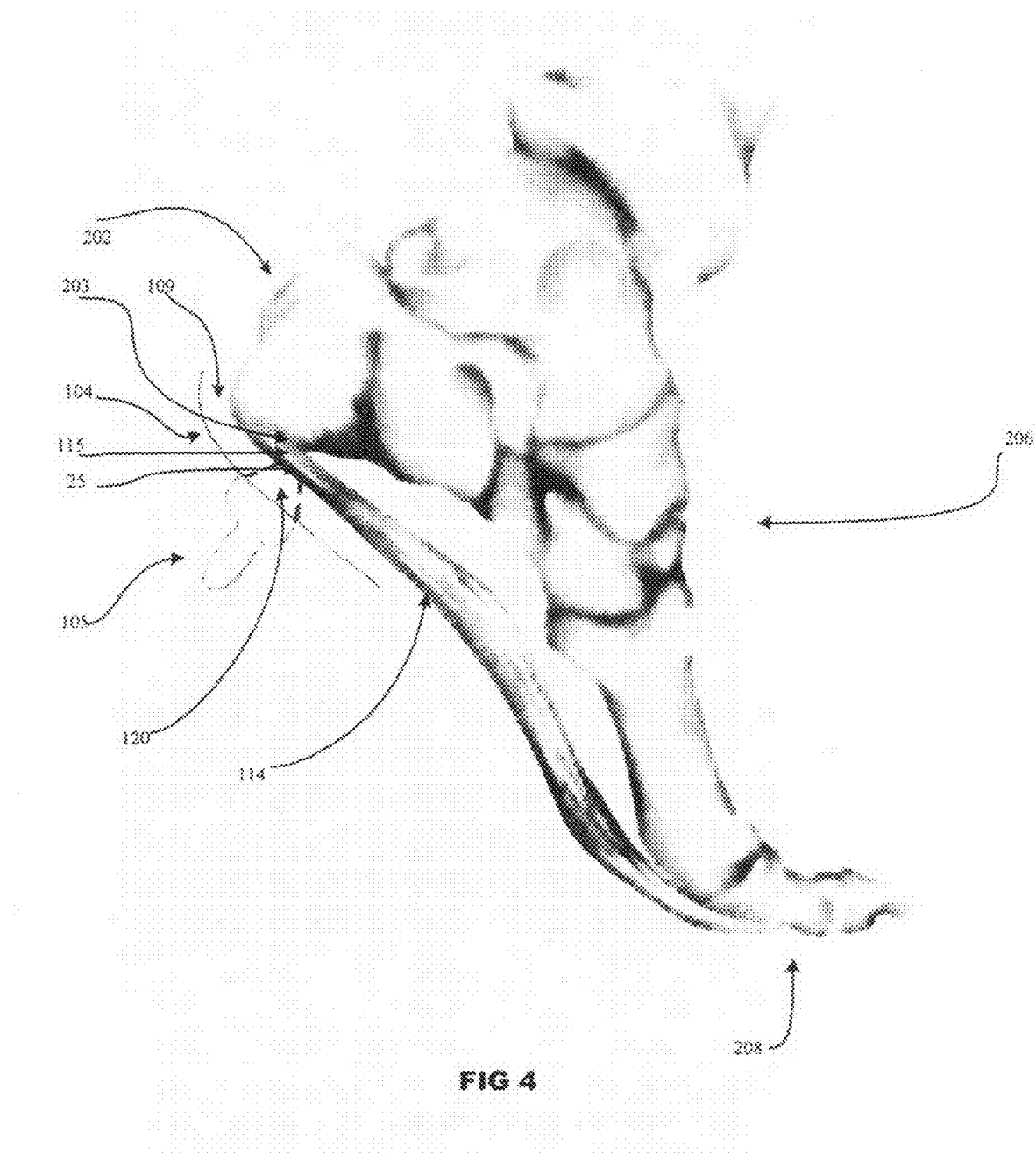
FIG. 4 illustrates a method of treating plantar fascia, according to various embodiments.

Now with reference to FIG. 4, plantar fasciitis is a painful condition caused by overuse of the plantar fascia 112 or arch tendon of the foot. The plantar fascia 112 is a broad, thick band of tissue that runs from under the heel 202 to the front of the foot 206. Plantar fasciitis is traditionally thought to be an inflammatory condition. The cause of pain and dysfunction can be degeneration of the collagen fibers 203 close to the attachment to the calcaneus (heel bone).

Longstanding cases of plantar fasciitis often demonstrate more degenerative changes than inflammatory changes, in which case they are termed plantar fasciosis, which is chronic degeneration without inflammation. Since tendons and ligaments do not contain blood vessels, they do not actually become inflamed. Instead, injury to the tendon is usually the result of an accumulation over time of microscopic tears at the cellular level.

Traditional surgical procedures, such as plantar fascia release, are a last resort, and often lead to further complications such as a lowering of the arch and pain in the side of the foot. Such surgical procedures will allow decompression of the nearby muscles that are inflamed. Such surgical procedures will not fix the underlying problem but will allow more space for the inflamed muscle, thus, relieving pain/pressure.

According to various embodiments, methods of treating plantar fascia 112 are provided. Such a method can include targeting the collagen fibers 203 within the plantar fascia 112 in ROI 115, directing therapeutic ultrasound energy 120 to the inflammatory cells within plantar fascia 112 to create one or more conformal regions of elevated temperature 25. The method can include ablating at least a portion of the collagen fibers 203 within plantar fascia 112, and improving collagen fibers 203. The method can include coupling ultrasound probe 105 to ROI 115. The method can include focusing therapeutic ultrasound energy 120 to create conformal region of elevated temperature 25 in a portion of collagen fibers 203. The method can include creating a plurality of conformal region of elevated temperature 25 in collagen fibers 203, which can be lesions in one embodiment. The method can include creating the plurality of region of elevated temperature 25 in a pattern, such as, a linear pattern, a 2-D pattern, or a 3-D pattern, and combinations thereof. The method further comprising measuring a distance on skin surface 104 and then directing therapeutic ultrasound energy 120 to collagen fibers 203. The method can also include imaging collagen fibers 203 within the plantar fascia 112. The method can also include imaging collagen fibers 203 after the ablating at least a portion of collagen fibers 203. The method can include comparing a measurement of collagen fibers 203 within the plantar fascia 112 before and after the ablating step. The method can include directing acoustical pressure or cavitation to the collagen fibers 203 after the ablating step further improving collagen fibers 203. The method can include increasing blood perfusion to ROI 115. The method can include administering a medicant to ROI 115. The method can also include any of the steps of method 100.

Figure 5:
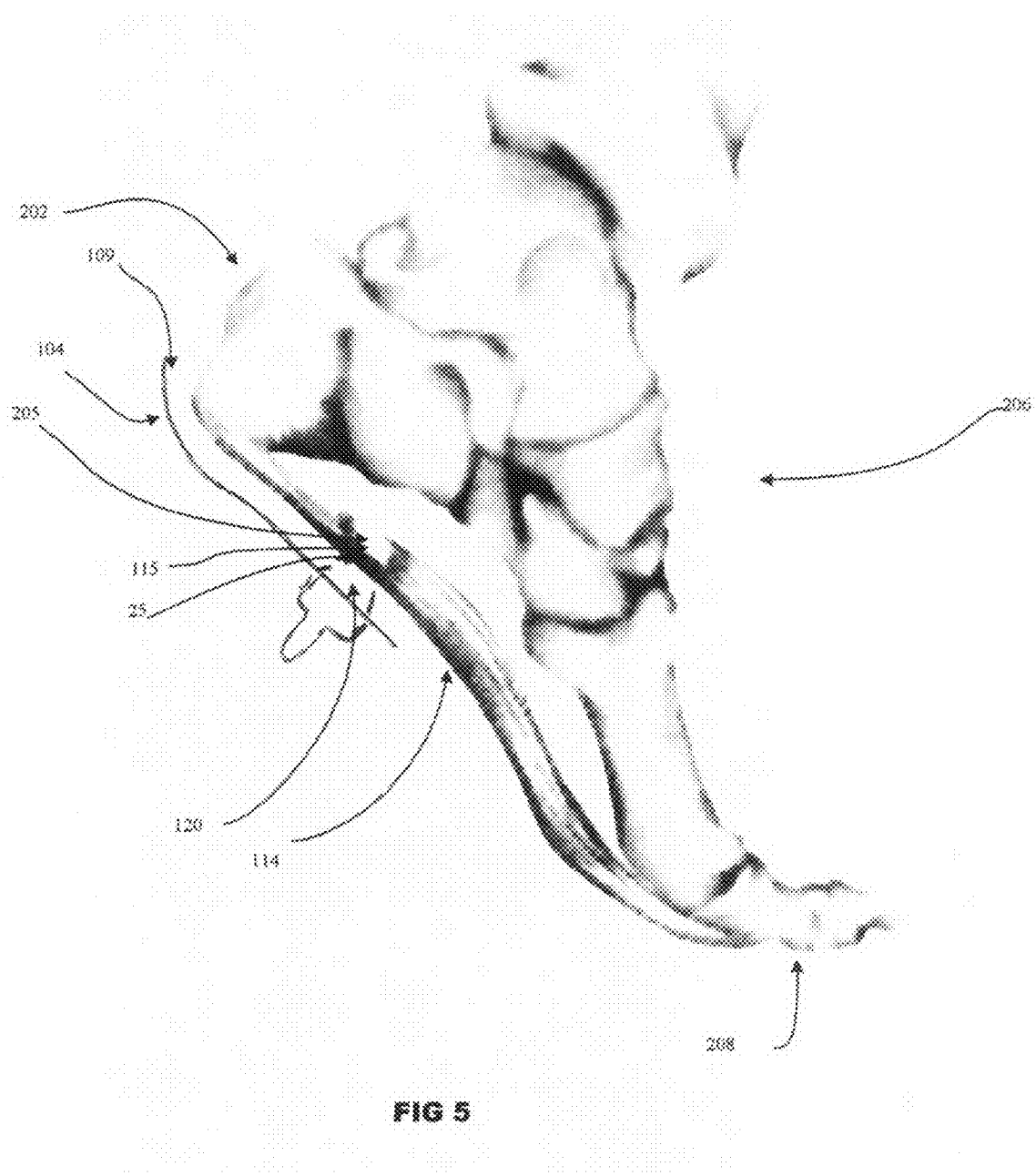
FIG. 5 illustrates a method of treating plantar fascia strains or ruptures, according to various embodiments.

Now referencing FIG. 5, plantar fascia 112 or arch ligament is a band that runs from under the heel to the front of the foot 206. A strain or rupture 205 to this is quite common. A plantar fascia strain might result from one single traumatic incident (an acute injury) or may gradually occur over a period of time (a chronic injury).

According to various embodiments, methods of treating plantar fascia 112 strains or ruptures 205 are provided. Such a method can include targeting the strain or rupture 205 within the plantar fascia 112 in ROI 115, directing therapeutic ultrasound energy 120 to the strainor rupture 205, to create one or more conformal regions of elevated temperature 25. The method can include ablating at least a portion of the strainor rupture 205, and improving strainor rupture 205 within plantar fascia 112. The method can include coupling ultrasound probe 105 to ROI 115. The method can include focusing therapeutic ultrasound energy 120 to create a region of elevated temperature 25 in a portion of the strainor rupture 205. The method can include creating a plurality of conformal region of elevated temperature 25 in the strainor rupture 205, which in one embodiment can be a plurality of lesions. The method can include creating the plurality of region of elevated temperature 25 in a pattern, such as, a linear pattern, a 2-D pattern, or a 3-D pattern, and combinations thereof. The method further comprising measuring a distance on skin surface 104 and then directing t ultrasound energy 120 to the strain or rupture 205. The method can also include imaging the strain or rupture 205 within plantar fascia 112. The method can also include imaging the strain or rupture 205 within plantar fascia 112 after the ablating at least a portion of the strain or rupture 205. The method can include comparing a measurement of the strain or rupture 205 within t plantar fascia 112 before and after the ablating step. The method can include directing acoustical pressure or cavitation to the strain or rupture 205 after the ablating step further improving strain or rupture 205 within the fascia 204. The method can include welding the rupture 205 with therapeutic ultrasound energy 120 to repair plantar fascia 112. The method can include increasing blood perfusion to ROI 115. The method can include administering a medicant to ROI 115. The method can also include any of the steps of method 100.

Figure 6A:
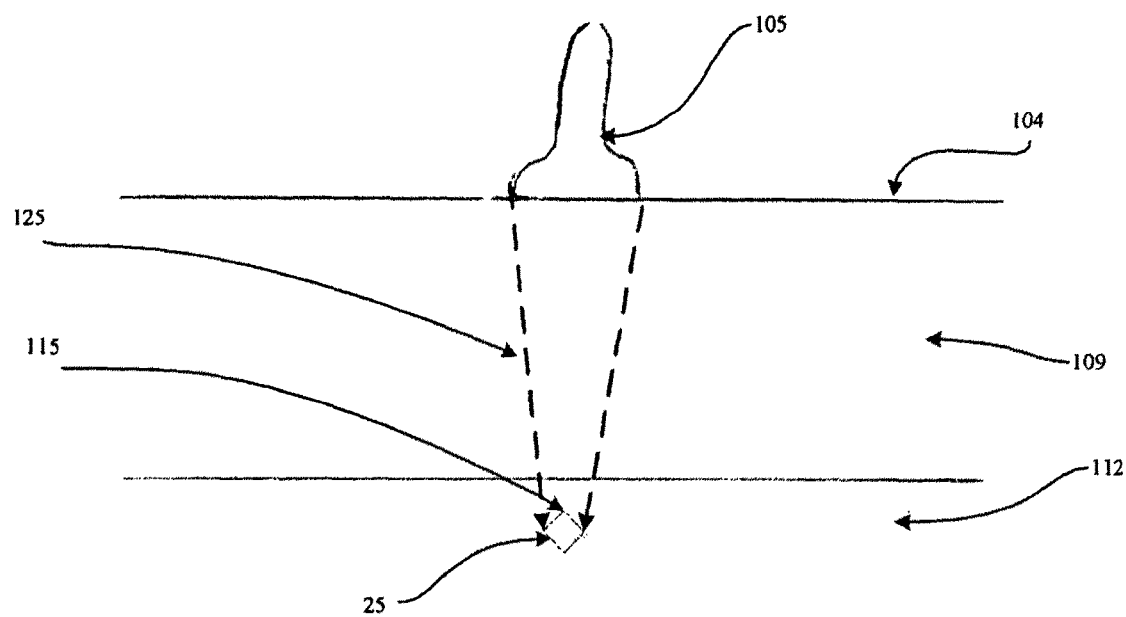
Figure 6B:
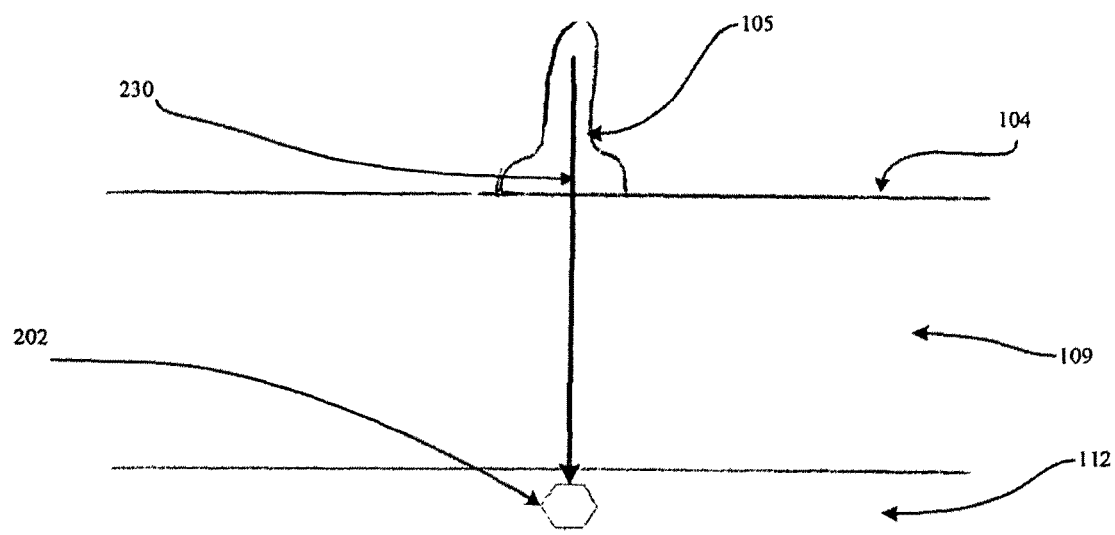
Figure 6C:
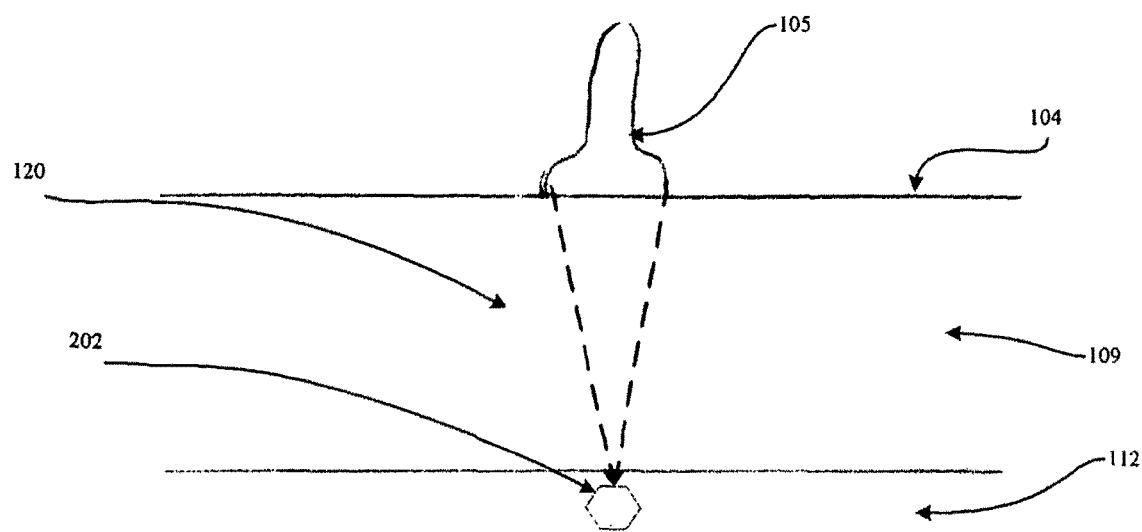

With reference to FIGS. 6A-C, method and system for treating injuries to plantar fascia 112 are illustrated. According to various embodiments, plantar fascia 112 located below surface 104. Between plantar fascia 112 and surface 104 is subcutaneous tissue 109 which can comprise plantar fascia 112. As discussed herein, subcutaneous tissue 109 can comprise various layers such as an epidermal layer, a dermal layer, a fat layer, a SMAS layer, connective tissue, and/or muscle. In various embodiments, probe 105 can be coupled to surface 104 and can emit ultrasound energy 125 into ROI 115. In various embodiments, a method can comprise imaging ROI 115 and in some embodiments, ROI 115 can comprise plantar fascia 112.

In various embodiments, needle 230 can be inserted through surface 104 and employed to direct medicant 202 to plantar fascia 112. In other embodiments, ultrasound energy can create a pressure gradient to direct medicant 202 through surface 104 to plantar fascia 112. In various embodiments, therapeutic ultrasound energy 120 is directed to plantar fascia 112. In various embodiments, ultrasound energy 120 create conformal region of elevated temperature 25 in a portion of planter fascia 112. In one embodiment, therapeutic ultrasound energy 120 can ablate a portion of plantar fascia 112. The one embodiment, therapeutic ultrasound energy 120 can be focused to a portion of plantar fascia 112. In one embodiment, therapeutic ultrasound imaging 120 can create a lesion in a portion of plantar fascia 112. In one embodiment, therapeutic ultrasound energy can coagulate a portion of plantar fascia 112. In one embodiment, therapeutic ultrasound energy 120 can weld a portion of plantar fascia 112, such as for example tendon 138. In one embodiment, therapeutic ultrasound energy 120 increases blood perfusion to plantar fascia 112. In one embodiment, therapeutic ultrasound energy accelerates inflammation peaking which may stimulate healing in plantar fascia 112. In one embodiment, therapeutic ultrasound energy 120 activates medicant 202. For example, medicant 202 can be one of Etanercept, Abatacept, Adalimumab, or Infliximab, which is direct to plantar fascia 112 and therapeutic ultrasound energy 125 can be directed to the plantar fascia 112 to improve plantar fascia 112. A second medicant 202 can be PRP which is directed to plantar fascia 112 following the therapeutic ultrasound energy 125. In a further example, therapeutic ultrasound energy 125 can be directed to the plantar fascia 112 to activate the PRP and improve plantar fascia 112.

Medicant 202 can be any chemical or naturally occurring substance that has an active component. For example a medicant 202 can be, but not limited to, a pharmaceutical, a drug, a medication, a vaccine, an antibody, a nutriceutical, an herb, a vitamin, a cosmetic, an amino acid, a protein, a sugar, a recombinant material, a collagen derivative, blood, blood components, somatic cell, gene therapy, tissue, recombinant therapeutic protein, stem cells, a holistic mixture, an anti-inflammatory, or combinations thereof or mixtures thereof. Medicant 202 can also include a biologic, such as for example a recombinant DNA therapy, synthetic growth hormone, monoclonal antibodies, or receptor constructs or combinations thereof or mixtures thereof. Medicant 202 can be any medicant, as described herein.

Medicant 202 can be administered by applying it to the skin surface 104 above ROI 115. Medicant 202 can be driven into subcutaneous tissue below the skin surface 104 by ultrasound energy 120. The ultrasound energy 120 may be provide mechanical motion, such as, vibrational, cavitation, harmonics, and/or pressure gradients, or provide a thermal gradient. A medicant 202 can be mixed in a coupling gel or can be used as a coupling gel. The medicant 202 can be administered to the circulatory system. For example, the medicant 202 can be in the blood stream and can be activated or moved to ROI 115 by the ultrasound energy 120. Medicant 202 can be administered by injection into or near ROI 115. The medicant 202 can be activated by ultrasound energy 120.

Figure 7A:
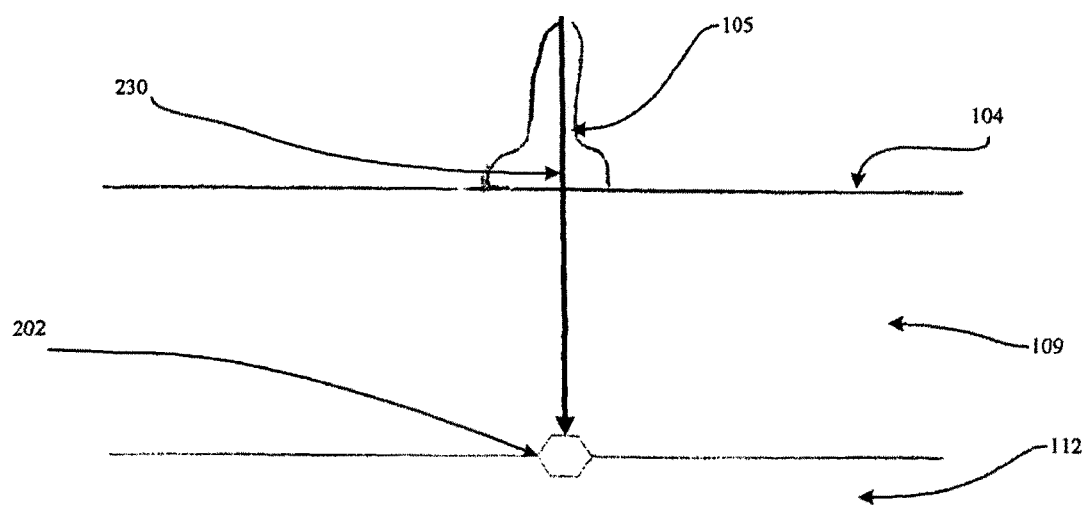
Figure 7B:
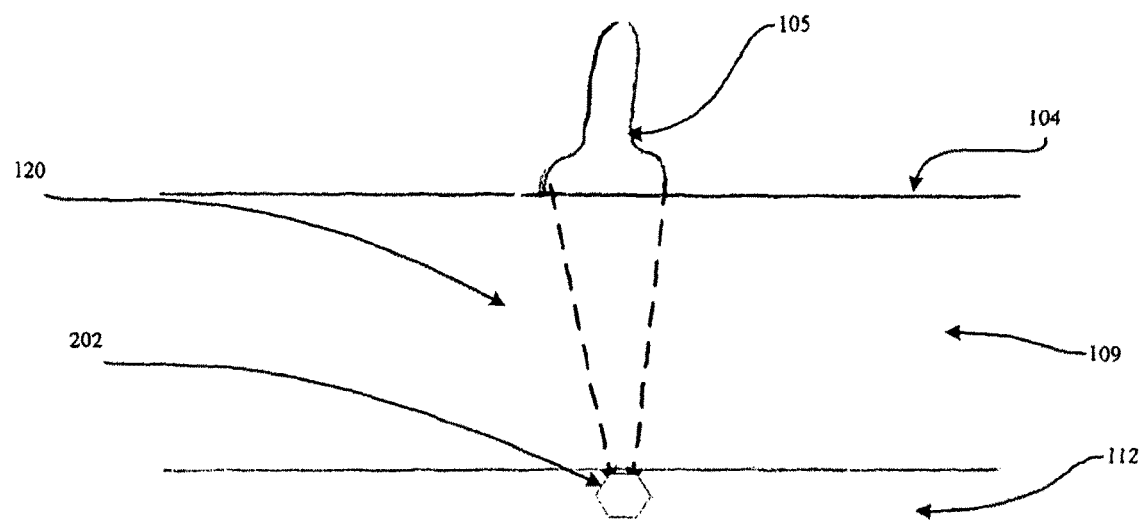
Figure 8A:
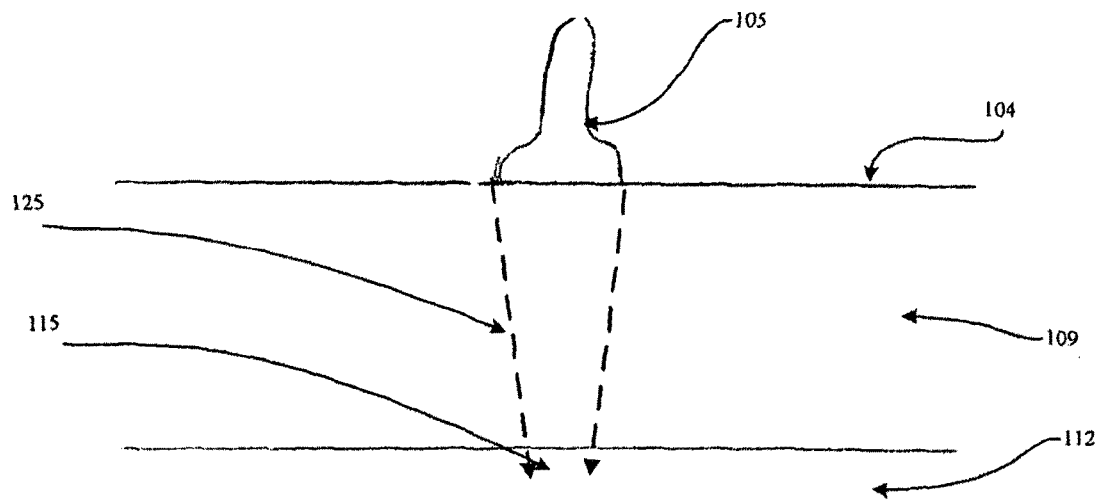
Figure 8B:
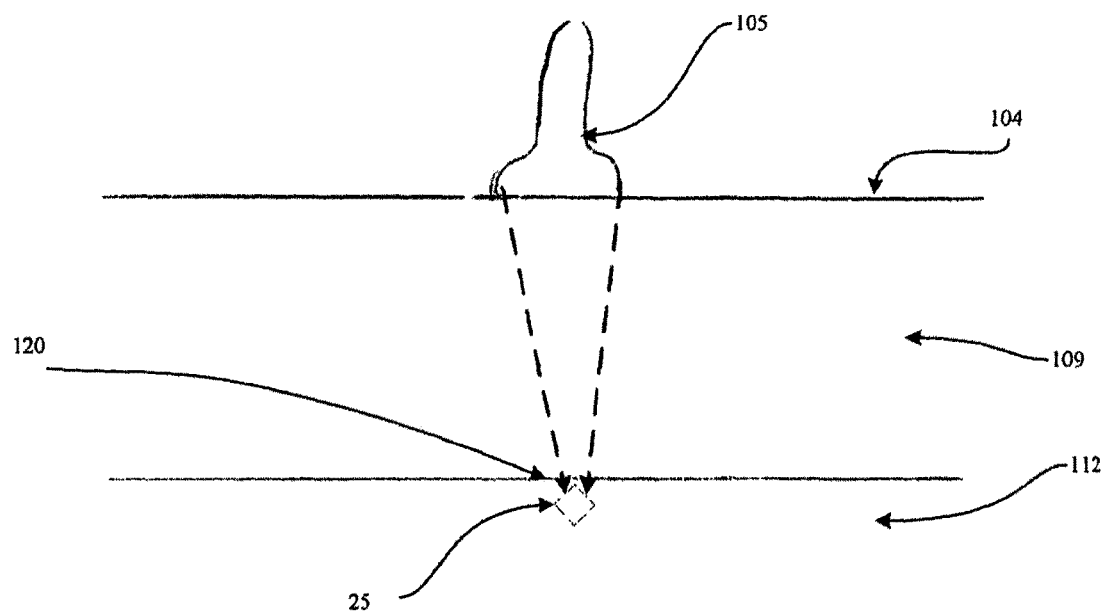
Figure 8C:
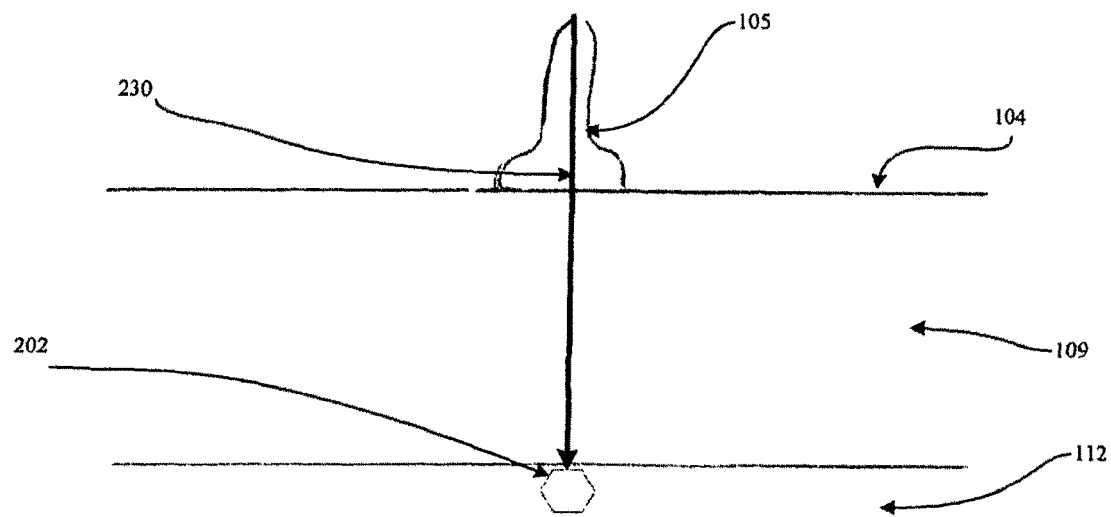
Figure 8D:
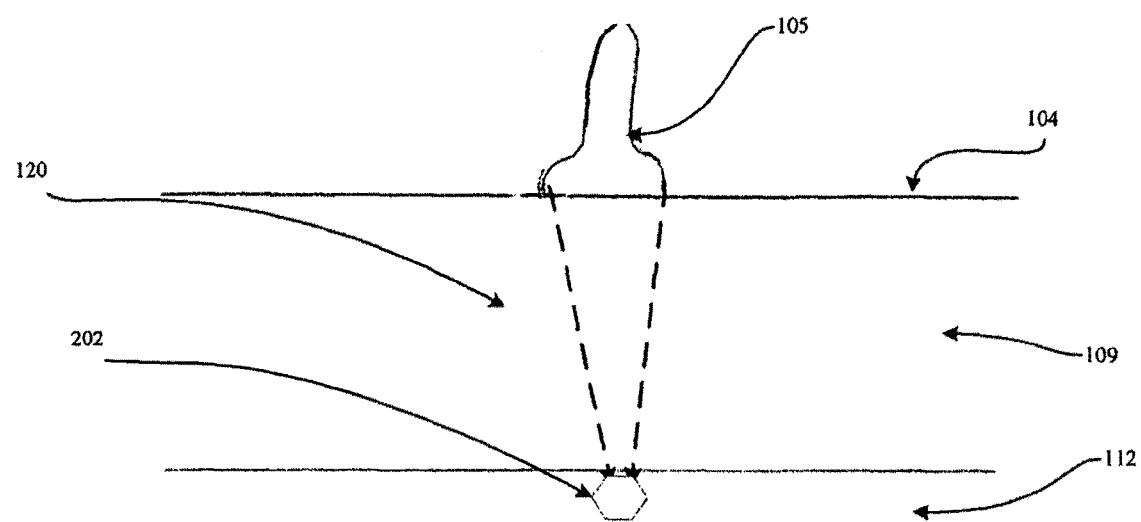

With reference to FIGS. 7A-B, method and system for treating injuries to plantar fascia 112 are illustrated. According to various embodiments, plantar fascia 112 located below surface 104. In various embodiments, needle 230 can be inserted through surface 104 and employed to direct medicant 202 to plantar fascia 112. In other embodiments, ultrasound energy 120 can create a pressure gradient to direct medicant 202 through surface 104 to plantar fascia 112. In various embodiments, therapeutic ultrasound energy 120 is directed to plantar fascia 112. In various embodiments, ultrasound energy 120 create conformal region of elevated temperature 25 in a portion of planter fascia 112. In one embodiment, therapeutic ultrasound energy 120 can ablate a portion of plantar fascia 112. The one embodiment, therapeutic ultrasound energy 120 can be focused to a portion of plantar fascia 112. In one embodiment, therapeutic ultrasound imaging 120 can create a lesion in a portion of plantar fascia 112. In one embodiment, therapeutic ultrasound energy can coagulate a portion of plantar fascia 112. In one embodiment, therapeutic ultrasound energy 120 can weld a portion of plantar fascia 112. In one embodiment, therapeutic ultrasound energy 120 increases blood perfusion to plantar fascia 112. In one embodiment, therapeutic ultrasound energy accelerates inflammation peaking which may stimulate healing in plantar fascia 112. In one embodiment, therapeutic ultrasound energy 120 activates medicant 202.

Moving to FIGS. 8A-D, method and system for treating injuries to plantar fascia 112 are illustrated. According to various embodiments, plantar fascia 112 is located below surface 104. Between plantar fascia 112 and surface 104 is subcutaneous tissue 109 which can comprise plantar fascia 112. In various embodiments, therapeutic ultrasound energy 120 is directed to plantar fascia 112. In one embodiment, therapeutic ultrasound energy 120 can ablate a portion of plantar fascia 112. The one embodiment, therapeutic ultrasound energy 120 can be focused to a portion of plantar fascia 112. In one embodiment, therapeutic ultrasound imaging 120 can create a lesion in a portion of plantar fascia 112. In one embodiment, therapeutic ultrasound energy can coagulate a portion of plantar fascia 112. In one embodiment, therapeutic ultrasound energy 120 can weld a portion of plantar fascia 112, such as for example tendon 138. In one embodiment, therapeutic ultrasound energy 120 increases blood perfusion to plantar fascia 112. In one embodiment, therapeutic ultrasound energy accelerates inflammation peaking which may stimulate healing in plantar fascia 112.

In various embodiments, needle 230 can be inserted through surface 104 and employed to direct medicant 202 to plantar fascia 112. In other embodiments, ultrasound energy 120 can create a pressure gradient to direct medicant 202 through surface 104 to plantar fascia 112. In various embodiments, therapeutic ultrasound energy 120 is directed to plantar fascia 112. In various embodiments, ultrasound energy 120 create conformal region of elevated temperature 25 in a portion of planter fascia 112. In one embodiment, therapeutic ultrasound energy 120 can ablate a portion of plantar fascia 112. The one embodiment, therapeutic ultrasound energy 120 can be focused to a portion of plantar fascia 112. In one embodiment, therapeutic ultrasound imaging 120 can create a lesion in a portion of plantar fascia 112. In one embodiment, therapeutic ultrasound energy can coagulate a portion of plantar fascia 112. In one embodiment, therapeutic ultrasound energy 120 can weld a portion of plantar fascia 112. In one embodiment, therapeutic ultrasound energy 120 increases blood perfusion to plantar fascia 112. In one embodiment, therapeutic ultrasound energy accelerates inflammation peaking which may stimulate healing in plantar fascia 112. In one embodiment, therapeutic ultrasound energy 120 activates medicant 202.

Now referring to FIG. 9, a method of treating injury to plantar fascia 112 is illustrated. In some embodiments, a method can optionally include imaging 702 of damage location in plantar fascia 112. In various embodiments, a method can include placing or directing a medicant 704 to damage location in plantar fascia 112. In some embodiments, a method can optionally include directing therapeutic ultrasound energy 705 to the site before the placing or directing a medicant 704 to damage location in plantar fascia 112. In various embodiments, a method can include directing therapeutic ultrasound energy 706 to damage location in plantar fascia 112. In various embodiments, a method can include stimulating or activating 708 at least one of medicant and surrounding tissue in the damage location in plantar fascia 112. In some embodiments, a method can optionally include directing a second energy 712 to damage location in plantar fascia 112 after include directing therapeutic ultrasound energy 706 to damage location in plantar fascia 112. In various embodiments, method can include improving plantar fasciitis or plantar fasciosis 710. In some embodiments, a method can include imaging damage location in plantar fascia 112 715 after stimulating or activating 708 at least one of medicant and surrounding tissue in damage location in plantar fascia 112. In some embodiments, the method can include placing a second medicant 719 to damage location in plantar fascia 112, then directing therapeutic ultrasound energy 706 to damage location in plantar fascia 112. In some embodiments, after imaging 715 of damage location in plantar fascia 112, a decision 717 can be made to loop back and repeat certain steps of method as described herein. As will be apparent to those skilled in the art, hashed lines and hashed boxes indicate steps which are optional in method 700.

In various embodiments, method 700 can treat either recent (acute injuries) or older injuries (chronic injuries), or combinations thereof. Inflammation can be classified as either acute or chronic, as described herein. In various embodiments, method 700 can treat chronic inflammation. In various embodiments, method 700 can treat acute inflammation. In some embodiments, method 700 can treat a combination of acute and chronic inflammation.

In various embodiments, method 700 can include improving plantar fasciitis and/or plantar fasciosis 710, which can include initiating or stimulating a biological effect. A biological effect can be stimulating or increase an amount of heat shock proteins. Such a biological effect can cause white blood cells to promote healing of a portion of the subcutaneous layer in damage location in plantar fascia 112. A biological effect can be to restart or increase the wound healing cascade in damage location in plantar fascia 112. A biological effect can be increasing the blood perfusion in damage location in plantar fascia 112. A biological effect can be encouraging collagen growth. A biological effect may increase the liberation of cytokines and may produce reactive changes in damage location in plantar fascia 112. A biological effect may by peaking inflammation in damage location in plantar fascia 112. A biological effect may be the disruption or modification of biochemical cascades. A biological effect may be the production of new collagen in damage location in plantar fascia 112. A biological effect may be a stimulation of cell growth in damage location in plantar fascia 112. A biological effect may be angiogenesis. A biological effect may be stimulation or activation of coagulation factors in damage location in plantar fascia 112. A biological effect may a cell permeability response. A biological effect may be an enhanced delivery of medicants to damaged location in plantar fascia 112.

In various embodiments, therapeutic ultrasound energy changes at least one of concentration and activity of inflammatory mediators (TNF-A, IL-1) as well as growth factors (TGF-B1, TGF-B3) in damage location in plantar fascia 112. In various embodiments, therapeutic ultrasound energy accelerates inflammation peaking, which can accelerate various healing cascades damage location in plantar fascia 112.

In various embodiments, method 700 can include improving plantar fasciitis and/or plantar fasciosis 710, which can include stimulating a change in at least one of concentration and activity damage location in plantar fascia 112 of one or more of the following: Adrenomedullin (AM), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumour necrosis factor-alpha (TNF-α), Vascular endothelial growth factor (VEGF), Wnt Signaling Pathway, placental growth factor (PlGF), [(Foetal Bovine Somatotrophin)] (FBS), IL-1—Cofactor for IL-3 and IL-6, which can activate T cells, IL-2—T-cell growth factor, which can stimulate IL-1 synthesis and can activate B-cells and NK cells, IL-3, which can stimulate production of all non-lymphoid cells, IL-4—Growth factor for activating B cells, resting T cells, and mast cells, IL-5, which can induce differentiation of activated B cells and eosinophils, IL-6, which can stimulate Ig synthesis and growth factor for plasma cells, IL-7 growth factor for pre-B cells, and/or any other growth factor not listed herein, and combinations thereof.

Various embodiments provide methods and system for permanent pain relief in damage location in plantar fascia 112. Nerve near to plantar fascia 112 and nerve ending is proximate to a part of plantar fascia 112. In some embodiments, pain in plantar fascia 112 is generated by nerve ending.

In various embodiments, probe 105 can be coupled to surface 104 and can emit ultrasound energy 125 into ROI 115. In various embodiments, a method can comprise imaging ROI 115 and in some embodiments, ROI 115 can comprise plantar fascia 112. In some embodiments, ROI 115 can comprise nerve ending. In various embodiments, therapeutic ultrasound energy 120 is directed to nerve ending. In some embodiments, ultrasound energy 120 can create conformal region of elevated temperature 25 in nerve ending. In one embodiment, therapeutic ultrasound energy 120 can ablate nerve ending. The one embodiment, therapeutic ultrasound energy 120 can be focused to a portion of nerve ending. In one embodiment, therapeutic ultrasound imaging 120 can create a lesion in a portion of nerve ending. In some embodiments, therapeutic ultrasound imaging 120 can destroy nerve ending.

In various embodiments, destruction of nerve ending can provide permanent pain relief in plantar fascia 112. Nerve ending can be a sensory nerve and typically is not a nerve that controls motor function. In some embodiments, destruction of nerve ending can employ a combination of therapeutic ultrasound energy 120 and deposition of medicant 202, such as for example Botox, on nerve ending. In some embodiments, medicant 202 can be directed to surrounding tissue near nerve ending to stimulate healing of the tissue.

In various embodiments, needle 230 can be inserted through surface 104 and employed to direct medicant 202 to plantar fascia 112. In other embodiments, ultrasound energy 120 can create a pressure gradient to direct medicant 202 through surface 104 to plantar fascia 112. In various embodiments, therapeutic ultrasound energy 120 is directed to surrounding tissue near nerve ending. In some embodiments, ultrasound energy 120 can create conformal region of elevated temperature 25 in a portion surrounding tissue near nerve ending. In one embodiment, therapeutic ultrasound energy 120 can ablate a portion surrounding tissue near nerve ending. The one embodiment, therapeutic ultrasound energy 120 can be focused to a portion of surrounding tissue near nerve ending. In one embodiment, therapeutic ultrasound imaging 120 can create a lesion in a portion surrounding tissue near nerve ending. In one embodiment, therapeutic ultrasound energy 120 can coagulate a portion of surrounding tissue near nerve ending. In one embodiment, therapeutic ultrasound energy 120 increases blood perfusion to surrounding tissue near nerve ending. In one embodiment, therapeutic ultrasound energy accelerates inflammation peaking which may stimulate healing in surrounding tissue near nerve ending. In one embodiment, therapeutic ultrasound energy 120 activates medicant 202. For example, medicant 202 can be Botox, which is direct to nerve ending and therapeutic ultrasound energy 125 can be directed to the plantar fascia 112 to permanently remove pain from plantar fascia 112. A second medicant 202 can be a steroid which is directed to plantar fascia 112 following the therapeutic ultrasound energy 125. In a further example, therapeutic ultrasound energy 125 can be directed to the plantar fascia 112 to activate the steroid and improve an injury in a portion of plantar fascia 112.

The following patents and patent applications are incorporated by reference for any purpose: US Patent Application Publication No. 20050256406, entitled "Method and System for Controlled Scanning, Imaging, and/or Therapy" published Nov. 17, 2005; US Patent Application Publication No. 20060058664, entitled "System and Method for Variable Depth Ultrasound Treatment" published Mar. 16, 2006; US Patent Application Publication No. 20060084891, entitled Method and System for Ultra-High Frequency Ultrasound Treatment" published Apr. 20, 2006; U.S. Pat. No. 7,530,958, entitled "Method and System for Combined Ultrasound Treatment" issued May 12, 2009; US Patent Application Publication No. 2008071255, entitled "Method and System for Treating Muscle, Tendon, Ligament, and Cartilage Tissue" published Mar. 20, 2008; U.S. Pat. No. 6,623,430, entitled "Method and Apparatus for Safely Delivering Medicants to a Region of Tissue Using Imaging, Therapy, and Temperature Monitoring Ultrasonic System, issued Sep. 23, 2003; U.S. Pat. No. 7,571,336, entitled "Method and System for Enhancing Safety with Medical Peripheral Device by Monitoring if Host Computer is AC Powered" issued Aug. 4, 2009; and US Patent Application Publication No. 20080281255, entitled "Methods and Systems for Modulating Medicants Using Acoustic Energy" published Nov. 13, 2008.

It is believed that the disclosure set forth above encompasses at least one distinct invention with independent utility. While the invention has been disclosed in the exemplary forms, the specific embodiments thereof as disclosed and illustrated herein are not to be considered in a limiting sense as numerous variations are possible. The subject matter of the inventions includes all novel and non-obvious combinations and sub combinations of the various elements, features, functions and/or properties disclosed herein.

Various embodiments and the examples described herein are exemplary and not intended to be limiting in describing the full scope of compositions and methods of this invention. Equivalent changes, modifications and variations of various embodiments, materials, compositions and methods may be made within the scope of the present invention, with substantially similar results.

The invention claimed is:

1. A non-invasive method of treating a plantar fascia using an ultrasound treatment system, the method comprising:
   locating a damage location within the plantar fascia; and
   directing, non-invasively, using the ultrasound treatment system, a therapeutically effective amount of conformal distributions of ultrasound energy to the damage location within the plantar fascia or tissue within the plantar fascia surrounding the damage location, thereby creating a therapeutically effective amount of conformal regions of elevated temperature in the plantar fascia, thereby creating a therapeutically effective amount of micro-lesions in the plantar fascia.

2. The method according to claim 1, wherein locating the damage location comprises imaging the damage location.

3. The method according to claim 1, the method further comprising driving a medicant into the damage location with the therapeutically effective amount of conformal distributions of ultrasound energy.

4. The method according to claim 3, the method further comprising activating the medicant with the therapeutically effective amount of conformal distributions of ultrasound energy.

5. The method according to claim 1, the therapeutically effective amount of conformal distributions of ultrasound energy peaking inflammation and initiating a wound healing cascade in a subcutaneous tissue surrounding the damage location.

6. The method according to claim 1, the therapeutically effective amount of conformal distributions of ultrasound energy welding together a portion of the plantar fascia in the damage location.

7. The method according to claim 1, the therapeutically effective amount of conformal distributions of ultrasound energy stimulating collagen growth in the plantar fascia.

8. A method of non-invasive treatment of a plantar fascia using an ultrasound treatment system, the method comprising:
   locating a damage location within a plantar fascia, the damage location including a micro-tear; and
   directing, non-invasively, using the ultrasound treatment system, a therapeutically effective amount of conformal distributions of ultrasound energy to the plantar fascia at the damage location within the plantar fascia or tissue within the plantar fascia surrounding the damage location, thereby creating a therapeutically effective amount of micro lesions in the plantar fascia, the therapeutically effective amount of micro-lesions initiating healing of the micro tear.

9. The method according to claim 8, the therapeutically effective amount of conformal distributions of ultrasound energy welding together the micro-tear.

10. The method according to claim 8, the therapeutically effective amount of conformal distributions of ultrasound energy stimulating collagen growth in the plantar fascia.

11. The method according to claim 8, the therapeutically effective amount of conformal distributions of ultrasound energy increasing blood perfusion to the damage location.

12. The method according to claim 8, the method further comprising directing, using the ultrasound treatment system, a second and different therapeutically effective amount of conformal distributions of ultrasound energy to the plantar fascia at the damage location or surrounding tissue, thereby initiating a therapeutic effect on the plantar fascia.

13. The method according the claim 8, the therapeutically effective amount of conformal distributions of ultrasound energy creating a three dimensional matrix of micro lesions in the plantar fascia at the damage location.

14. A method of non-invasive treatment of a plantar fascia using an ultrasound transducer, the method comprising:
   coupling the ultrasound transducer to a tissue surface of a foot containing the plantar fascia, the ultrasound transducer configured to emit ultrasound energy;
   locating a micro-tear in the plantar fascia; and
   non-invasively focusing a therapeutically effective amount of conformal distributions of the ultrasound energy from the ultrasound transducer to the micro-tear in the plantar fascia, thereby creating a therapeutically effective amount of conformal regions of elevated temperature at the micro-tear in the plantar fascia, thereby welding the micro-tear, wherein the therapeutically effective amount of conformal regions of elevated temperature are placed at a selected depth below the tissue surface and have a defined shape and volume.

15. The method according to claim 14, the method further comprising imaging the damage location before and after creating the therapeutically effective amount of conformal regions of elevated temperature in the damage location.

16. The method according to claim 14, the therapeutically effective amount of conformal distributions of ultrasound energy ablating a portion of the plantar fascia.

17. The method according to claim 14, the method further comprising driving a medicant into the damage location with the therapeutically effective amount of conformal distributions of ultrasound energy.

18. The method according to claim 1, wherein the therapeutically effective amount of conformal regions of elevated temperature are placed at a selected depth below the surface of a foot and have a defined shape and volume.

* * * * *

UNITED STATES PATENT AND TRADEMARK OFFICE
CERTIFICATE OF CORRECTION

PATENT NO. : 10,183,182 B2
APPLICATION NO. : 13/136541
DATED : January 22, 2019
INVENTOR(S) : Michael H. Slayton et al.

Page 1 of 1

It is certified that error appears in the above-identified patent and that said Letters Patent is hereby corrected as shown below:

In the Specification

Column 18, Line 67, "ultrasbund" should be --ultrasound--.

Signed and Sealed this
Sixteenth Day of July, 2019

Andrei Iancu
*Director of the United States Patent and Trademark Office*